US011889861B2

(12) United States Patent
Hejazi et al.

(10) Patent No.: US 11,889,861 B2
(45) Date of Patent: Feb. 6, 2024

(54) ARRANGEMENT OF ATOMIZATION ASSEMBLIES FOR AEROSOL DELIVERY DEVICE

(71) Applicant: RAI STRATEGIC HOLDINGS, INC., Winston-Salem, NC (US)

(72) Inventors: Vahid Hejazi, Concord, NC (US); Rajesh Sur, Winston-Salem, NC (US); S Keith Cole, Advance, NC (US); Cassidy S. McMahan, Pfafftown, NC (US); Gary M. Dull, Lewisville, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 561 days.

(21) Appl. No.: 17/026,997

(22) Filed: Sep. 21, 2020

(65) Prior Publication Data

US 2021/0084970 A1 Mar. 25, 2021

Related U.S. Application Data

(60) Provisional application No. 62/904,249, filed on Sep. 23, 2019.

(51) Int. Cl.
*A24F 40/05* (2020.01)
*A24F 40/10* (2020.01)
*A61M 15/06* (2006.01)

(52) U.S. Cl.
CPC ............. *A24F 40/05* (2020.01); *A24F 40/10* (2020.01); *A61M 15/06* (2013.01)

(58) Field of Classification Search
CPC .......... A24F 40/05; A24F 40/10; A24F 42/20; A61M 11/005; A61M 15/0003;
(Continued)

(56) References Cited

U.S. PATENT DOCUMENTS 5,152,457 A * 10/1992 Burwell ............. B05B 17/0607
310/323.01
5,996,903 A 12/1999 Asai et al.
(Continued)

FOREIGN PATENT DOCUMENTS

| CN | 206423575 | 8/2017 |
| EP | 3228345 | 10/2017 |

(Continued)

OTHER PUBLICATIONS

Ding et al., "Surface acoustic wave microfluidics", The Royal Society of Chemistry, Jul. 2013, pp. 3626-3649.
(Continued)

*Primary Examiner* — Abdullah A Riyami
*Assistant Examiner* — Thang H Nguyen
(74) *Attorney, Agent, or Firm* — WOMBLE BOND DICKINSON (US) LLP

(57) ABSTRACT

The present disclosure provides an aerosol delivery device that may comprise a housing defining an outer wall. The device may further include a power source and a control component, an exit aerosol path defined through an opening, a tank portion that includes a reservoir configured to contain a liquid composition, and an atomization assembly configured to vaporize the liquid composition to generate an aerosol. The atomization assembly may comprise two or more vibrating assemblies each of which includes a mesh plate. In some implementations, the mesh plates may be substantially coplanar and substantially perpendicular to the exit aerosol path. In other implementations, the mesh plates may be non-coplanar.

25 Claims, 13 Drawing Sheets

(58) Field of Classification Search
CPC .......... A61M 15/0021; A61M 15/0085; A61M 15/06; A61M 2016/0024; A61M 2016/0027; A61M 2202/0007; A61M 2202/0468; A61M 2205/0211; A61M 2205/0238; A61M 2205/0294; A61M 2205/7536; A61M 2205/8206; A61M 2205/8243; A61M 2205/8262; A61M 2205/8293; A61M 2206/14; A61M 2209/06; A61M 2205/121; A61M 2205/123; A61M 2205/3317; A61M 2205/332; A61M 2205/3334; A61M 2205/3569; A61M 2205/3584; A61M 2205/3592; A61M 2205/3653; A61M 2205/505; A61M 2205/581; A61M 2205/582; A61M 2205/583; A61M 2205/588; A61M 2205/7527; A61P 25/26; B05B 17/0646; B05B 17/0661; B05B 17/0669; H01L 41/09

See application file for complete search history.

(56) References Cited

U.S. PATENT DOCUMENTS

| | | | |
|---|---|---|---|
| 8,998,483 | B2 | 4/2015 | Friend et al. |
| 9,420,829 | B2* | 8/2016 | Thorens ............... A24F 40/44 |
| 9,687,027 | B2* | 6/2017 | Poston ............... A61M 11/047 |
| 9,770,055 | B2 | 9/2017 | Cameron et al. |
| 9,848,648 | B2 | 12/2017 | Memari et al. |
| 9,867,398 | B2* | 1/2018 | Guo ............... B05B 17/0615 |
| 9,888,723 | B2* | 2/2018 | Cameron ............... A24F 40/46 |
| 9,936,737 | B2* | 4/2018 | Cameron ............... A24F 40/40 |
| 9,962,507 | B2* | 5/2018 | Germinario ......... A61M 16/108 |
| 10,004,259 | B2 | 6/2018 | Sebastian et al. |
| 10,564,655 | B2* | 2/2020 | Blackley ............ G01N 33/0036 |
| 2003/0150451 | A1* | 8/2003 | Shayan ............... A61M 11/042 |
| | | | 128/203.12 |
| 2006/0196518 | A1 | 9/2006 | Hon |
| 2008/0084134 | A1 | 4/2008 | Morita et al. |
| 2008/0217430 | A1 | 9/2008 | Feriani et al. |
| 2009/0151717 | A1 | 6/2009 | Bowen et al. |
| 2013/0213419 | A1 | 8/2013 | Tucker et al. |
| 2013/0319404 | A1 | 12/2013 | Feriani et al. |
| 2014/0238423 | A1 | 8/2014 | Tucker et al. |
| 2014/0261487 | A1 | 9/2014 | Chapman et al. |
| 2015/0034103 | A1* | 2/2015 | Hon ............... A24F 40/44 |
| | | | 131/328 |
| 2015/0101606 | A1 | 4/2015 | White |
| 2015/0117841 | A1 | 4/2015 | Brammer et al. |
| 2015/0238423 | A1 | 8/2015 | Wertz et al. |
| 2015/0245669 | A1* | 9/2015 | Cadieux ............... A24F 40/42 |
| | | | 131/329 |
| 2016/0213866 | A1* | 7/2016 | Tan ............... A61M 15/0021 |
| 2016/0271347 | A1* | 9/2016 | Raichman ......... A61M 15/0063 |
| 2016/0338407 | A1* | 11/2016 | Kerdemelidis ......... A24F 40/60 |
| 2016/0366946 | A1 | 12/2016 | Murison et al. |
| 2017/0042241 | A1* | 2/2017 | Murison ............... F04B 17/003 |
| 2017/0064997 | A1* | 3/2017 | Murison ............... H02J 7/0044 |
| 2017/0106153 | A1* | 4/2017 | Davidson .......... A61M 15/0013 |
| 2017/0157341 | A1* | 6/2017 | Pandya ............... A61M 15/009 |
| 2017/0238608 | A1* | 8/2017 | Matsumoto .......... A61M 11/006 |
| 2017/0303594 | A1* | 10/2017 | Cameron ............... A61M 15/00 |
| 2017/0318860 | A1* | 11/2017 | Adair ............... A24F 40/49 |
| 2017/0368273 | A1 | 12/2017 | Rubin |
| 2018/0038838 | A1 | 2/2018 | Karancsi et al. |
| 2018/0070638 | A1* | 3/2018 | Qiu ............... H02J 7/32 |
| 2018/0090923 | A1 | 3/2018 | Li et al. |
| 2018/0153217 | A1 | 6/2018 | Liu et al. |
| 2018/0161525 | A1* | 6/2018 | Liu ............... A61M 15/001 |
| 2018/0169682 | A1* | 6/2018 | Miller ............... B05B 17/0607 |
| 2018/0169691 | A1* | 6/2018 | Macloughlin ........ A61M 11/005 |
| 2018/0280633 | A1* | 10/2018 | Miller ............... A61M 11/003 |
| 2018/0289076 | A1* | 10/2018 | Manca ............... B05B 7/2464 |
| 2018/0289908 | A1* | 10/2018 | Marmur ............... A61M 11/001 |
| 2019/0014819 | A1 | 1/2019 | Sur |
| 2019/0124982 | A1* | 5/2019 | Atkins ............... A24F 40/30 |
| 2019/0125987 | A1 | 5/2019 | Germinario et al. |
| 2019/0200679 | A1* | 7/2019 | Dayioglu ............... A24F 7/00 |
| 2019/0209791 | A1* | 7/2019 | Courbat ............... A24F 40/50 |
| 2019/0321570 | A1* | 10/2019 | Rubin ............... A61M 16/209 |
| 2019/0343182 | A1* | 11/2019 | Yilmaz ............... A61M 15/06 |
| 2020/0276398 | A1 | 9/2020 | Hebrank et al. |
| 2021/0015158 | A1* | 1/2021 | Moloney ............... A24F 40/60 |

FOREIGN PATENT DOCUMENTS

| | | |
|---|---|---|
| EP | 3272237 | 1/2018 |
| EP | 3278678 | 2/2018 |
| EP | 3287019 | 2/2018 |
| EP | 3298912 | 3/2018 |
| EP | 3305104 | 4/2018 |
| JP | 2004-249208 A | 9/2004 |
| WO | WO2016165055 | 10/2016 |
| WO | WO2017051181 | 3/2017 |
| WO | WO2017063256 | 4/2017 |
| WO | WO2017149165 | 9/2017 |
| WO | WO2017175218 | 10/2017 |
| WO | WO2017201710 | 11/2017 |
| WO | WO2017201716 | 11/2017 |
| WO | WO2017202014 | 11/2017 |
| WO | WO2017206022 | 12/2017 |
| WO | WO2017206480 | 12/2017 |
| WO | WO2017215221 | 12/2017 |
| WO | WO2018000756 | 1/2018 |
| WO | WO2018000760 | 1/2018 |
| WO | WO2018000761 | 1/2018 |
| WO | WO2018000829 | 1/2018 |
| WO | WO2018001105 | 1/2018 |
| WO | WO2018001106 | 1/2018 |
| WO | WO2018023890 | 2/2018 |
| WO | WO2018040380 | 3/2018 |
| WO | WO2018053955 | 3/2018 |
| WO | WO2018058883 | 4/2018 |
| WO | WO2018058884 | 4/2018 |
| WO | WO2018095312 | 5/2018 |

OTHER PUBLICATIONS

Yeo et al., "Ultrafast microfluidics using surface acoustic waves", American Institute of Physics, 2009, pp. 1-23.

Qi et al., "Miniature inhalation therapy platform using surface acoustic wave microfluidic atomization", The Royal Society of Chemistry, May 2009, pp. 2184-2193.

Ariyakul et al., "Olfactory Display Using a Miniaturized Pump and a SAW Atomizer for Presenting Low-volatile Scents", IEEE Virtual Reality, 2011, pp. 193-194.

Olszewski et al., "A silicon-based MEMS vibrating mesh nebulizer for inhaled drug delivery", Procedia Engineering, 2016, pp. 1521-1524.

Hawkins et al., "Vibrating Mesh Nebulizer Reference Design", Microchip Technology Inc., 2016-2017, pp. 1-50.

Kesten et al., "Development of a novel digital breath-activated inhaler: Initial particle size characterization and clinical testing", Pulmonary Pharmacology & Therapeutics, Carlsbad, California, USA, 2018, pp. 27-32.

International Search Report from the corresponding International Application No. PCT/IB2020/058882, dated Dec. 23, 2020, 6 pages.

* cited by examiner

ARRANGEMENT OF ATOMIZATION ASSEMBLIES FOR AEROSOL DELIVERY DEVICE

CROSS-REFERENCE TO RELATED APPLICATIONS

This application claims priority to, and the benefit of, U.S. Provisional Patent Application No. 62/904,249, titled Arrangement of Atomization Assemblies for Aerosol Delivery Device, filed on Sep. 23, 2019, which is incorporated herein in its entirety by reference.

TECHNOLOGICAL FIELD

The present disclosure relates to aerosol delivery devices, and more particularly to an aerosol delivery device that includes a reservoir and an atomization assembly, which may utilize electrical power to vaporize an aerosol precursor composition for the production of an aerosol. In various implementations, the aerosol precursor composition, which may incorporate materials and/or components that may be made or derived from tobacco or otherwise incorporate tobacco or other plants, may include natural or synthetic components including flavorants, and/or may include one or more medicinal components, is vaporized by the atomization assembly to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., which are incorporated herein by reference in their entireties. See also, for example, the various types of smoking articles, aerosol delivery devices, and electrically powered sources referenced by brand name and commercial source in U.S. Pat. App. Pub. No. 2015/0216232 to Bless et al., which is incorporated herein by reference in its entirety.

However, it would be desirable to provide an aerosol delivery device with enhanced functionality. In this regard, it is desirable to provide an aerosol delivery with advantageous features.

BRIEF SUMMARY

The present disclosure relates to aerosol delivery devices, methods of forming such devices, and elements of such devices. One implementation of the present invention provides an aerosol delivery device that may comprise a housing defining an outer wall, and further including a power source and a control component, an exit aerosol path defined through an opening, a tank portion that includes a reservoir configured to contain a liquid composition, and an atomization assembly configured to vaporize the liquid composition to generate an aerosol. The atomization assembly may comprise two or more vibrating assemblies, at least one of which may be in fluid communication with the reservoir, each vibrating assembly may include a mesh plate, the mesh plates may be substantially coplanar, and the mesh plates may be substantially perpendicular to the exit aerosol path.

In some implementations, the mesh plates may be substantially linearly aligned. In some implementations, there may be three vibrating assemblies. In some implementations, the mesh plates of the three vibrating assemblies may be substantially linearly aligned. In some implementations, the mesh plates of the three vibrating assemblies may be radially spaced about a center of the device. In some implementations, the mesh plates of the three vibrating assemblies may be substantially evenly spaced. In some implementations, the housing may define an inner surface, and at least a portion of the inner surface may be coated with a hydrophobic coating. In some implementations, each of the vibrating assemblies may further include a piezoelectric ring affixed to and substantially surrounding the mesh plate. In some implementations, each of the mesh plates may be substantially flat. In some implementations, at least a portion of each of the mesh plates may be convex with respect to the reservoir. Some implementations may further comprise a mouthpiece portion, and the opening may be defined in the mouthpiece portion.

Another implementation of the present invention provides an aerosol delivery device that may comprise a housing defining an outer wall, and further including a power source and a control component, an exit aerosol path defined through an opening, a tank portion that includes a reservoir configured to contain a liquid composition, and an atomization assembly configured to vaporize the liquid composition to generate an aerosol. The atomization assembly may comprise two or more vibrating assemblies, at least one of which may be in fluid communication with the reservoir, each vibrating assembly may include a mesh plate, and the mesh plates may be substantially non-coplanar.

In some implementations, there may be two vibrating assemblies, the mesh plates of the vibrating assemblies may be located on opposite sides of the exit aerosol path, and at least one of the mesh plates of the vibrating assemblies may define an acute angle with respect to a portion of the exit aerosol path proximate the opening. In some implementations, there may be two vibrating assemblies, the mesh plates of the vibrating assemblies may be located on opposite sides of the exit aerosol path, and at least one of the mesh plates of the vibrating assemblies may define an obtuse angle with respect to a portion of the exit aerosol path proximate the opening. In some implementations, there may be two vibrating assemblies, the opening may be offset from the center of the device, the mesh plates of the vibrating assemblies may be substantially parallel, and each of the mesh plates of the vibrating assemblies may define an acute angle with respect to a portion of the exit aerosol path proximate the opening. In some implementations, the mesh plates of the vibrating assemblies may be angled toward the opening.

In some implementations, there may be two vibrating assemblies, the mesh plates of the vibrating assemblies may be substantially parallel and may be positioned one above the other, and the mesh plates of the vibrating assemblies may be substantially perpendicular to the exit aerosol path.

In some implementations, both of the vibrating assemblies may be in fluid communication with the liquid composition. In some implementations, a first one of the vibrating assemblies may be in fluid communication with the liquid composition and may be configured to generate a first aerosol, the first aerosol may create a thin film on a second one of the vibrating assemblies, and the second one of the vibrating assemblies may be configured to re-aerosolize the thin film of liquid composition to generate a second aerosol. In some implementations, there may be two vibrating assemblies, and the mesh plates of the vibrating assemblies may be substantially parallel to the exit aerosol path. In some implementations, the housing may define an inner surface, and at least a portion of the inner surface may be coated with a hydrophobic coating. In some implementations, each of the vibrating assemblies may further include a piezoelectric ring affixed to and substantially surrounding the mesh plate. In some implementations, each of the mesh plates is substantially flat. In some implementations, at least a portion of each of the mesh plates may be convex with respect to the reservoir. Some implementations may further comprise a mouthpiece portion, and the opening may be defined in the mouthpiece portion.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWINGS

In order to assist the understanding of aspects of the disclosure, reference will now be made to the appended drawings, which are not necessarily drawn to scale and in which like reference numerals refer to like elements. The drawings are provided by way of example to assist understanding of aspects of the disclosure, and should not be construed as limiting the disclosure.

DETAILED DESCRIPTION

Figure 1:
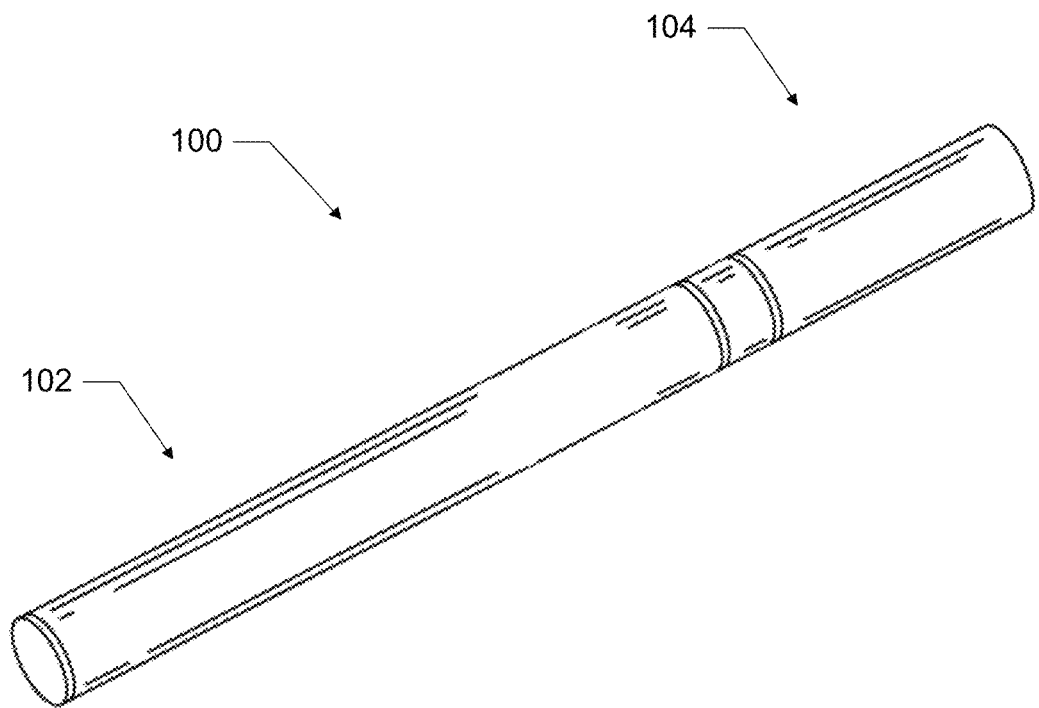
FIG. 1 is a perspective schematic view of an aerosol delivery device, according to an example implementation of the present disclosure.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to vaporize a material (preferably without combusting the material to any significant degree and/or without significant chemical alteration of the material) to form an inhalable substance; and components of such devices have the form of articles that most preferably are sufficiently compact to be considered hand-held devices. That is, use of components of some aerosol delivery devices does not result in the production of smoke—i.e., from by-products of combustion or pyrolysis of tobacco, but rather, use of those preferred systems results in the production of vapors resulting from vaporization of an aerosol precursor composition. In some examples, components of aerosol delivery devices may be characterized as electronic cigarettes, and those electronic cigarettes most preferably incorporate tobacco and/or components derived from tobacco, and hence deliver tobacco derived components in aerosol form. It will be appreciated, however, that devices in accordance with various embodiments can be used to deliver active ingredients other than nicotine and/or tobacco components. Other examples include delivery devices for botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)).

Aerosol generating devices of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use the device much like a smoker employs a traditional type of smoking article, draw on one end of that device for inhalation of aerosol produced by that device, take or draw puffs at selected intervals of time, and the like.

Aerosol delivery devices of the present disclosure also may be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power, such as by controlling electrical current flow the power source to other components of the article—e.g., a microcontroller or microprocessor), an atomization assembly, a liquid composition (e.g., commonly an aerosol precursor composition liquid capable of yielding an aerosol, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated may be withdrawn therefrom upon draw).

Alignment of the components within the aerosol delivery device may be variable. In specific embodiments, the aerosol precursor composition may be located between two opposing ends of the device (e.g., within a reservoir of a cartridge, which in certain circumstances is replaceable and disposable or refillable). Other configurations, however, are not excluded. Generally, the components are configured relative to one another so that energy from the atomization assembly vaporizes the aerosol precursor composition (as well as one or more flavorants, medicaments, or the like that may likewise be provided for delivery to a user) and forms an aerosol for delivery to the user. When the atomization assembly vaporizes the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

More specific formats, configurations and arrangements of components within the aerosol delivery devices of the present disclosure will be evident in light of the further disclosure provided hereinafter. Additionally, the selection and arrangement of various aerosol delivery device components may be appreciated upon consideration of the commercially available electronic aerosol delivery devices, such as those representative products referenced in the background art section of the present disclosure.

Figure 2:
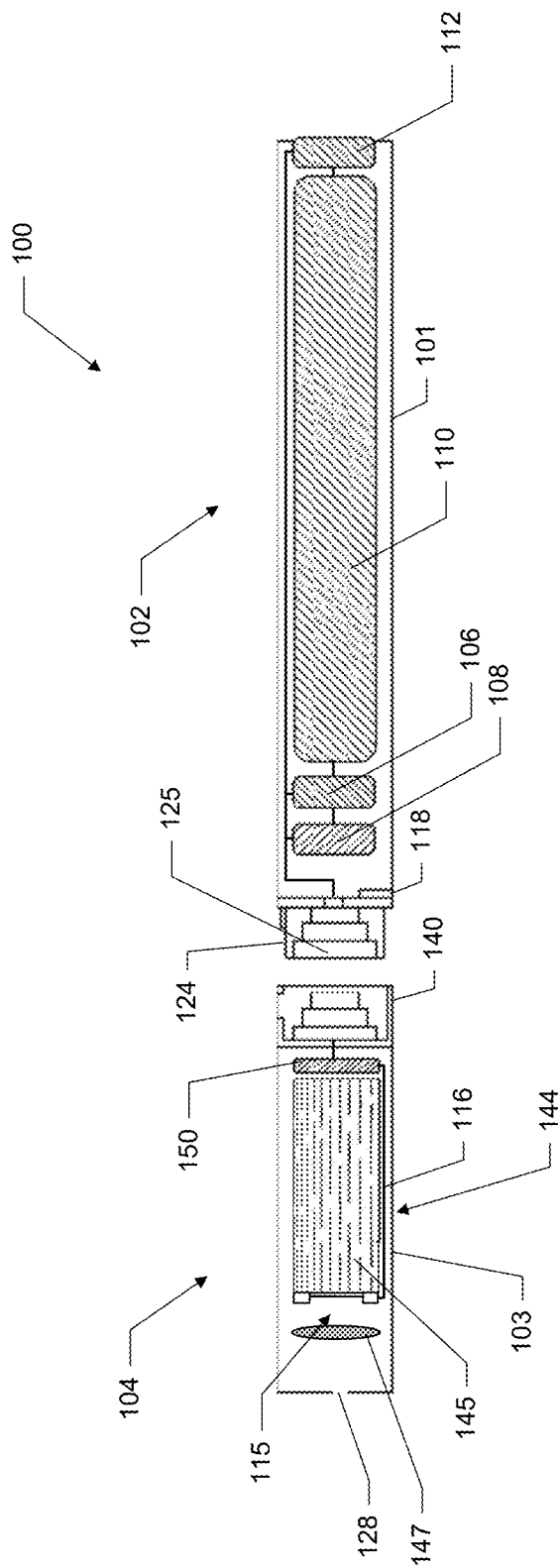
FIG. 2 illustrates a front cross-section schematic view of an aerosol delivery device, according to an example implementation of the present disclosure.

FIG. 1 illustrates an aerosol delivery device, according to an example implementation of the present disclosure. In particular, FIG. 1 illustrates a perspective schematic view of an aerosol delivery device 100 comprising a cartridge 104 and a control unit 102. As depicted in the figure, the cartridge 104 may be permanently or detachably aligned in a functioning relationship with the control unit 102. In some implementations, for example, the cartridge and the control unit may comprise a single part, whereas in other implementations (such as the depicted implementation), a connection therebetween may be releasable such that, for example, the control unit may be reused with one or more additional cartridges that may be disposable and/or refillable. In other implementations, the cartridge may not be linearly aligned with the control unit, such as implementations in which the cartridge and the control unit are in a side-by-side arrangement. In various implementations, a variety of different means of engagement may be used to couple a cartridge and a control unit together. For example, in some implementations the cartridge and the control unit may be coupled via one or more of a snap fit engagement, a press fit engagement, a threaded engagement, and a magnetic engagement. It should be noted that the components depicted in this and the other figures are representative of the components that may be present in a control unit and/or cartridge and are not intended to limit the scope of the control unit and/or cartridge components that are encompassed by the present disclosure. Some examples of mechanical and electrical connections between a cartridge and a control unit are described in U.S. patent application Ser. No. 16/386,940, filed on Apr. 17, 2019, and titled Connectors for Forming Electrical and Mechanical Connections Between Interchangeable Units in an Aerosol Delivery System, the disclosure of which is incorporated herein by reference in its entirety. FIG. 2 illustrates a front cross-section schematic view of the aerosol delivery device 100.

As depicted, the cartridge 104 and control unit 102 of FIG. 1 are shown in a de-coupled configuration. In various implementations, the aerosol delivery device 100 may have a variety of different shapes. For example, in some implementations (such as the depicted implementation) the aerosol delivery device 100 may be substantially rod-like or substantially tubular shaped or substantially cylindrically shaped. In other implementations, however, other shapes and dimensions are possible (e.g., rectangular, oval, hexagonal, prismatic, regular or irregular polygon shapes, disc-shaped, cube-shaped, multifaceted shapes, or the like). In still other implementations, the cartridge and the control unit may have different shapes. It should be noted for purposes of the present disclosure that the term "substantially" should be understood to mean approximately and/or within a certain degree of manufacturing tolerance as would be understood by one skilled in the art.

In the depicted implementation, the control unit 102 and the cartridge 104 include components adapted to facilitate mechanical engagement therebetween. Although a variety of other configurations are possible, the control unit 102 of the depicted implementation includes a coupler 124 that defines a cavity 125 therein. Likewise, the cartridge 104 includes a base 140 adapted to engage the coupler 124 of the control unit 102. A coupler and a base that may be useful according to the present disclosure are described in U.S. Pat. App. Pub. No. 2014/0261495 to Novak et al., the disclosure of which is incorporated herein by reference in its entirety.

It should be noted, however, that in other implementations various other structures, shapes, and/or components may be employed to couple the control unit and the cartridge. For example, in some implementations the control unit and cartridge may be coupled together via an interference or press fit connection such as, for example, implementations wherein the control body includes a chamber configured to receive at least a portion of the cartridge or implementations wherein the cartridge includes a chamber configured to receive at least a portion of the control unit. In other implementations, the cartridge and the control unit may be coupled together via a screw thread connection. In still other implementations, the cartridge and the control unit may be coupled together via a bayonet connection. In still other implementations, the cartridge and the control unit may be coupled via a magnetic connection. In various implementations, once coupled an electrical connection may be created between the cartridge and the control unit so as to electrically connect the cartridge (and components thereof) to the power source and/or via the control component of the control unit. Such an electrical connection may exist via one or more components of the coupling features. In such a manner, corresponding electrical contacts in the cartridge and the control unit may be substantially aligned after coupling to provide the electrical connection.

In specific implementations, one or both of the control unit 102 and the cartridge 104 may be referred to as being disposable or as being reusable. For example, in some implementations the control unit may have a power source. In some implementations, the power source may comprise a replaceable battery or a rechargeable battery and thus may be combined with any type of recharging technology, including connection to a wall charger, connection to a car charger (e.g., cigarette lighter receptacle, USB port, etc.), connection to a computer, any of which may include a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In some implementations, the power source may comprise a photovoltaic system. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

As illustrated in the figure, the control unit 102 may be formed of a control unit housing 101 that includes a control component 106 (e.g., a printed circuit board (PCB), an integrated circuit, a memory component, a microcontroller, or the like), a flow sensor 108, a battery 110, and a light-emitting diode (LED) 112, which components may be variably aligned. Some example types of electronic components, structures, and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference in their entireties. Some examples of batteries that may be applicable to the present disclosure are described in U.S. Pat. App. Pub. No. 2010/0028766 to Peckerar et al., the disclosure of which is incorporated herein by reference in its entirety. In some implementations, further indicators (e.g., a haptic feedback component, an audio feedback component, or the like) may be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties. It should be understood that in various implementations not all of the illustrated elements may be required. For example, in some implementations an LED may be absent or may be replaced with a different indicator, such as a vibrating indicator. Likewise, a flow sensor may be replaced with a manual actuator, such as, for example, one or more manually actuated push buttons.

In the depicted implementation, the cartridge 104 may be formed of a cartridge housing 103, which may define a liquid reservoir 144 configured to contain a liquid composition 145. In some implementations, the liquid reservoir may be part of the cartridge housing (such as, for example, comprising a molded feature of the cartridge housing), while in other implementations, the liquid reservoir may comprise a separate part. In some implementations, the liquid reservoir may be disposable. In other implementations, the liquid reservoir may be refillable. In various implementations, the liquid composition contained in the liquid reservoir 144 may comprise an aerosol precursor composition. Some examples of types of substrates, reservoirs, or other components for supporting a liquid composition are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety.

In some implementations, the reservoir may be made of a polymeric material that, in further implementations, may be at least partially transparent or translucent. In some implementations, such materials, may include, but need not be limited to, polycarbonate, acrylic, polyethylene terephthalate (PET), amorphous copolyester (PETG), polyvinyl chloride (PVC), liquid silicone rubber (LSR), cyclic olefin copolymers, polyethylene (PE), ionomer resin, polypropylene (PP), fluorinated ethylene propylene (FEP), styrene methyl methacrylate (SMMA), styrene acrylonitrile resin (SAN), polystyrene, acrylonitrile butadiene styrene (ABS), and combinations thereof. Other materials may include, for example, biodegradable polymers such as, but not limited to, polylactcic acid (PLA), polyhydroxyalkanoates (PHA's), and polybutylene succinate (PBS). In some implementations, the reservoir may be made of other material that may be at least partially transparent or translucent. Such materials may include, for example, glass or ceramic materials.

In some implementations, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. App. Pub. No. 2015/0335070 to Sears et al., the disclosure of which is incorporated herein by reference in its entirety. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine, USP/EP nicotine, etc.). In other implementations, non-tobacco materials alone may form the aerosol precursor composition. In some implementations, the aerosol precursor composition may include tobacco-extracted nicotine with tobacco or non-tobacco flavors and/or non-tobacco-extracted nicotine with tobacco or non-tobacco flavors.

In the depicted implementation, the liquid composition, sometimes referred to as an aerosol precursor composition or a vapor precursor composition or "e-liquid", may comprise a variety of components, which may include, by way of example, a polyhydric alcohol (e.g., glycerin, propylene glycol, or a mixture thereof), nicotine, tobacco, tobacco extract, and/or flavorants. Representative types of aerosol precursor components and formulations are also set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating device provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating device. In one or more embodiments, about 1 ml or more, about 2 ml or more, about 5 ml or more, or about 10 ml or more of the aerosol precursor composition may be included.

In the some of the examples described above, the aerosol precursor composition comprises a glycerol-based liquid. In other implementations, however, the aerosol precursor composition may be a water-based liquid. In some implementations, the water-based liquid may be comprised of more than approximately 80% water. For example, in some implementations the percentage of water in the water-based liquid may be in the inclusive range of approximately 90% to approximately 93%. In some implementations, the water-based liquid may include up to approximately 10% propylene glycol. For example, in some implementations the percentage of propylene glycol in the water-based liquid may be in the inclusive range of approximately 4% to approximately 5%. In some implementations, the water-based liquid may include up to approximately 10% flavorant. For example, in some implementations the percentage of flavorant(s) of the water-based liquid may be in the inclusive range of approximately 3% to approximately 7%. In some implementations, the water-based liquid may include up to approximately 1% nicotine. For example, in some implementations the percentage nicotine in the water-based liquid may be in the inclusive range of approximately 0.1% to approximately 0.3%. In some implementations, the water-based liquid may include up to approximately 10% cyclodextrin. For example, in some implementations the percentage cyclodextrin in the water-based liquid may be in the inclusive range of approximately 3% to 5%. In still other implementations, the aerosol precursor composition may be a combination of a glycerol-based liquid and a water-based liquid. For example, some implementations may include up to approximately 50% water and less than approximately 20% glycerol. The remaining components may include one or more of propylene glycol, flavorants, nicotine, cyclodextrin, etc. Some examples of water-based liquid compositions that may be suitable are disclosed in GB 1817863.2, filed Nov. 1, 2018, titled Aerosolisable Formulation; GB 1817864.0, filed Nov. 1, 2018, titled Aerosolisable Formulation; GB 1817867.3, filed Nov. 1, 2018, titled Aerosolisable Formulation; GB 1817865.7, filed Nov. 1, 2018, titled Aerosolisable Formulation; GB 1817859.0, filed Nov. 1, 2018, titled Aerosolisable Formulation; GB 1817866.5, filed Nov. 1, 2018, titled Aerosolisable Formulation; GB 1817861.6, filed Nov. 1, 2018, titled Gel and Crystalline Powder; GB 1817862.4, filed Nov. 1, 2018, titled Aerosolisable Formulation; GB 1817868.1, filed Nov. 1, 2018, titled Aerosolised Formulation; and GB 1817860.8, filed Nov. 1, 2018, titled Aerosolised Formulation, each of which is incorporated by reference herein in its entirety.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In various implementations, the aerosol precursor composition may include nicotine. In some implementations, nicotine incorporated in the aerosol precursor composition may include nicotine derived from non-tobacco plant sources, such as other members of the Solanaceae family. The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)).

As noted above, various implementations, the liquid composition may include a flavorant. In some implementations, the flavorant may be pre-mixed with the liquid. In other implementations, the flavorant may be delivered separately downstream from the atomizer as a main or secondary flavor. Still other implementations may combine a pre-mixed flavorant with a downstream flavorant. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime, lemon, mango, and other citrus flavors), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, ginseng, chamomile, turmeric, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Other examples include flavorants derived from, or simulating, burley, oriental tobacco, flue cured tobacco, etc. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

Referring back to FIG. 2, the liquid reservoir 144 of the depicted implementation may be in fluid communication with (either directly or through one or more additional components) at least a portion of an atomization assembly 115. In some implementations, the liquid reservoir 144 may comprise an independent container (e.g., formed of walls substantially impermeable to the liquid composition). In some implementations, the walls of the liquid reservoir may be flexible and/or collapsible, while in other implementations the walls of the liquid reservoir may be substantially rigid. In some implementations, the liquid reservoir may be substantially sealed to prevent passage of the liquid composition therefrom except via any specific openings or conduits provided expressly for passage of the liquid composition, such as through one or more transport elements as otherwise described herein.

An electrical connection 116 connects the atomization assembly 115 to the base 140 of the cartridge 104, which, when assembled to the control unit 102, provides an electrical connection to the control component 106 and/or the battery 110. As noted, the atomization assembly 115 is configured to be electrically connected to the battery 110 and/or the control component 106. In such a manner, the atomization assembly 115 of the depicted implementation may be energized by the battery 110 and/or control component 106 (e.g., so as to vibrate a component of the atomization assembly at a relatively high rate). In various implementations, an atomization assembly 115 may be fluidly coupled with a portion of the liquid composition such that the atomization assembly 115 generates an aerosol from the liquid composition. In various implementations, an atomization assembly may be directly fluidly coupled with a portion of the liquid composition, or indirectly fluidly coupled with a portion of the liquid composition, such as via a liquid transport element. In various implementations, a liquid transport element may have one layer, or multiple layers, and may be made of a single material or multiple materials. In various implementations, the liquid transport element may be any shape and may be a porous, semi-porous, or non-porous absorbent/adsorbent material. In other implementations, there may be a second liquid transport element located between the first liquid transport element and the liquid reservoir, the second liquid transport element being configured to transfer liquid from the liquid reservoir to the first liquid transport element. In such a manner, the first liquid transport element may not be in direct contact with the liquid in the liquid reservoir. In various implementations, the second liquid transport element may be made of the same material or a different material than the first liquid transport element and may have a shape that is the same or differs from that of the first liquid transport element.

For example, in some implementations the liquid transport element may be made of fibrous materials (e.g., organic cotton, cellulose acetate, regenerated cellulose fabrics, glass fibers), polymers, silk, particles, porous ceramics (e.g., alumina, silica, zirconia, SiC, SiN, AlN, etc.), porous metals, porous carbon, graphite, porous glass, sintered glass beads, sintered ceramic beads, capillary tubes, porous polymers, or the like. In some implementations, the liquid transport element may be any material that contains an open pore network (i.e., a plurality of pores that are interconnected so that fluid may flow from one pore to another in a plurality of direction through the element). The pores can be nanopores, micropores, macropores or combinations thereof. As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. In some embodiments, the liquid transport element may be a substantially solid non-porous material, such as a polymer or dense ceramic or metals, configured to channel liquid through apertures or slots while not necessarily relying upon wicking through capillary action. Such a solid body may be used in combination with a porous absorptive pad. The absorptive pad may be formed of silica-based fibers, organic cotton, rayon fibers, cellulose acetate, regenerated cellulose fabrics, highly porous ceramic or metal mesh, etc. Some representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials that may be suitable for use according to embodiments of the present disclosure are described, for example, in U.S. Pat. App. Pub. No. 2017/0188626 to Davis et al., and U.S. Pat. App. Pub. No. 2014/0123989 to LaMothe, the disclosures of which are incorporated herein by reference in their entireties. In some implementations, the porous monolith may form a substantially solid wick.

In various implementations, an end of the liquid transport element may be configured to be placed proximate the mesh plate and between the mesh plate and liquid composition in the reservoir so that the liquid transport element acts as a secondary reservoir that absorbs or adsorbs the liquid from the reservoir so that the mesh plate is in contact with the liquid composition, even if there is no longer liquid in the reservoir. In such a manner, the liquid transport element is configured to facilitate contact between the liquid composition and the atomization assembly.

In some implementations, the liquid composition may be driven through a component of the atomization assembly resulting in the generation of a plurality of aerosol particles. Likewise, in other implementations, vibration of a component of the atomization assembly may create ultrasonic waves within the liquid composition and/or surface acoustic waves in the liquid composition, that result in the formation of an aerosol at the surface of the liquid composition. As will be described in more detail below, in some implementations the liquid composition may be applied and/or transferred to a component of the atomization assembly to create the aerosol.

In the depicted implementation, the control unit housing 101 includes an air intake 118, which may comprise an opening in the housing proximate the coupler 124 allowing for passage of ambient air into the control unit housing 101 where it then passes through the cavity 125 of the coupler 124, and eventually into or around the atomization assembly 115, where it may be mixed with the vaporized aerosol precursor composition to comprise the aerosol that is delivered to the user. It should be noted that in other implementations the air intake 118 is not limited being on or adjacent the control unit housing 101, and, in some implementations, may be located downstream from the atomization assembly. In some implementations, an air intake may be formed through the cartridge housing 103 (e.g., such that it does not enter the control unit 102) or some other portion of the aerosol delivery device 100. In the depicted implementation, a mouthpiece portion that includes an opening 128 may be present in the cartridge housing 103 (e.g., at a mouthend of the cartridge 104) to allow for egress of the formed aerosol from the cartridge 104, such as for delivery to a user drawing on the mouthend of the cartridge 104. It should be noted that some implementations need not include a mouthpiece portion and/or the mouthpiece portion may be integral with a control unit or a cartridge. As such, in some implementations the opening may be defined in the control unit or the cartridge.

In various implementations, the cartridge 104 may also include at least one electronic component 150, which may include an integrated circuit, a memory component, a sensor, or the like, although such a component need not be included.

In those implementations that include such a component, the electronic component 150 may be adapted to communicate with the control component 106 and/or with an external device by wired or wireless means. In various implementations, the electronic component 150 may be positioned anywhere within the cartridge 104 or its base 140. Some examples of electronic/control components that may be applicable to the present disclosure are described in U.S. Pat. App. Pub. No. 2019/0014819 to Sur, which is incorporated herein by reference in its entirety. Although in the depicted implementation the control component 106 and the flow sensor 108 are illustrated separately, it should be noted that in some implementations the control component and the flow sensor may be combined as an electronic circuit board with the air flow sensor attached directly thereto. In some embodiments, the air flow sensor may comprise its own circuit board or other base element to which it can be attached. In some embodiments, a flexible circuit board may be utilized. A flexible circuit board may be configured into a variety of shapes, include substantially tubular shapes. Configurations of a printed circuit board and a pressure sensor, for example, are described in U.S. Pat. App. Pub. No. 2015/0245658 to Worm et al., the disclosure of which is incorporated herein by reference. Additional types of sensing or detection mechanisms, structures, and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some implementations, when a user draws on the article 100, airflow may be detected by the sensor 108, and the atomization assembly 115 may be activated, which may vaporize the liquid composition. As noted above, in some implementations drawing upon the mouthend of the article 100 causes ambient air to enter the air intake 118 and pass through the cavity 125 in the coupler 124 and the base 140. In the cartridge 104, the drawn air combines with the formed vapor to form the aerosol. The aerosol is whisked, aspirated, or otherwise drawn away from the atomization assembly 115 and out of the mouth opening 128 in the mouthend of the article 100. As noted, in other implementations, in the absence of an airflow sensor, the atomization assembly 115 may be activated manually, such as by a push button (not shown). Additionally, in some implementations, the air intake may occur through the cartridge or between the cartridge and the control unit. It should be noted that in some implementations, there may be one or more components between the atomization assembly and the opening in the mouthend of the article. For example, in the depicted implementation a heating component 147 is located downstream from the atomization assembly 115. In various implementations, the heating component may comprise any device configured to elevate the temperature of the generated aerosol, including, for example, one or more coil heating components, ceramic heating components, etc.

In some implementations, one or more input elements may be included with the aerosol delivery device (and may replace or supplement an airflow sensor, pressure sensor, or manual push button). In various implementations, an input element may be included to allow a user to control functions of the device and/or for output of information to a user. Any component or combination of components may be utilized as an input for controlling the function of the device. For example, one or more pushbuttons may be used as described in U.S. Pat. App. Pub. No. 2015/0245658 to Worm et al., which is incorporated herein by reference in its entirety.

Likewise, a touchscreen may be used as described in U.S. patent application Ser. No. 14/643,626, filed Mar. 10, 2015, to Sears et al., which is incorporated herein by reference in its entirety. As a further example, components adapted for gesture recognition based on specified movements of the aerosol delivery device may be used as an input. See U.S. App. Pub. No. 2016/0158782 to Henry et al., which is incorporated herein by reference in its entirety. As still a further example, a capacitive sensor may be implemented on the aerosol delivery device to enable a user to provide input, such as by touching a surface of the device on which the capacitive sensor is implemented.

In some embodiments, an input element may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pat. App. Pub. No. 2016/0007561 to Ampolini et al., the disclosure of which is incorporated herein by reference in its entirety. In such implementations, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

Yet other features, controls or components that may be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In various implementations, the atomization assembly may comprise a variety of different components or devices configured to generate an aerosol from the liquid composition. For example, in some implementations the atomization assembly may comprise a jet nebulizer assembly, which may be configured to utilize compressed air to generate an aerosol. In other implementations, the atomization assembly may comprise an ultrasonic assembly, which may be configured to utilize the formation of ultrasonic waves within the liquid composition to generate an aerosol. In other implementations, the atomization assembly may comprise a vibrating mesh assembly, which may comprise a piezoelectric material (e.g., a piezoelectric ceramic material) affixed to and substantially surrounding a mesh plate, (e.g., a perforated plate such as a micro-perforated mesh plate) that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In some implementations, the atomization assembly may comprise a surface acoustic wave (SAW) or Raleigh wave assembly, which may utilize surface wave characteristics to generate an aerosol at the surface of the liquid composition. It should be noted that for purpose of this application, an ultrasonic assembly may be any assembly configured to create ultrasonic waves within the liquid composition. In some implementations, for example, a vibrating mesh assembly may also operate as an ultrasonic assembly.

Figure 3:
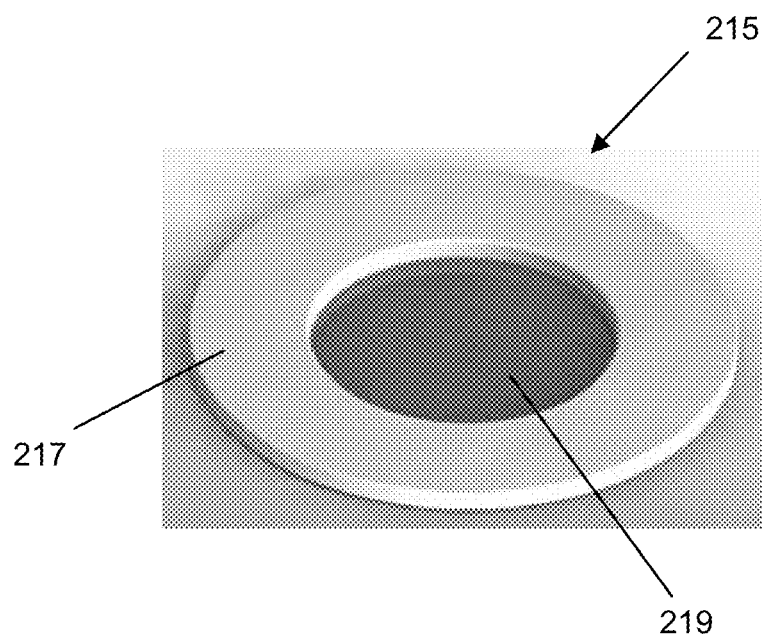
FIG. 3 illustrates a perspective view of a portion of an atomization assembly, according to an example implementation of the present disclosure.

An example of an atomization assembly of one implementation is shown in FIG. 3. In particular, FIG. 3 illustrates an atomization assembly 215 that comprises a piezoelectric ring 217 affixed to and substantially surrounding a mesh plate 219. In some implementations, additional components may be included. For example, in some implementations a supporting component may be included that is located on the side of the mesh plate opposite the vibrating component (e.g., such that the mesh plate is sandwiched between the supporting component and the vibrating component). Although other configurations are possible, in some implementations, the supporting component may comprise a supporting ring. In various implementations, the supporting component may be made of any suitable material, including, but not limited to, polymeric, metal, and/or ceramic materials. In such a manner, in some implementations the supporting component may increase the longevity of the mesh plate. In some implementations, the supporting component may be replaceable, while in other implementations the supporting component may be affixed to the mesh plate and/or the vibrating component. In some implementations, an auxiliary component may be used that is located between mesh plate and the vibrating component. Although other configurations are possible, in some implementations, the auxiliary component may comprise an auxiliary ring. In various implementations, the auxiliary component may be made of any suitable material, including, but not limited to, polymeric, metal, and/or ceramic materials. In such a manner, the auxiliary component may facilitate the interfacial contact of the components. In some implementations, the auxiliary component may be replaceable, while in other implementations the auxiliary component may be affixed to the mesh plate and/or the vibrating component.

In various implementations, the piezoelectric ring (or other component) may be affixed to the mesh plate in a variety of ways, including, for example, by gluing the components together via epoxy or other adhesive, including, for example, low mechanical damping adhesives, which may aid in efficiently transferring the applied vibration to the mesh plate. In other implementations, the components may be affixed to each other in other ways, including, for example, by ultrasonic welding, mechanical fasteners, etc. It should be noted that while the depicted implementation describes a piezoelectric component in the form of a piezoelectric ring, in other implementations the piezoelectric component need not be limited to a ring-shaped object. For example, in some implementations the piezoelectric component may have rectangular, oval, hexagonal, triangular, and regular or irregular polygon shapes. In various implementations, the mesh plate may have a variety of different configurations. For example, in some implementations the mesh plate may have a substantially flat profile. In other implementations, the mesh plate may have a substantially domed shape, which may be concave or convex with respect to the liquid composition. In other implementations, the mesh plate may include a substantially flat portion and a domed portion. In various implementations, the mesh plate may be made of a variety of different materials. In some implementations, the mesh plate may be made of a metal material, such as, but not limited to, stainless steel, palladium-nickel, or titanium. In other implementations, the mesh plate may be made of a polymeric material, such as, for example, a polyimide polymer. In still other implementations, the mesh plate may be made of a combination of materials.

In some implementations, one or both sides of the mesh plate may include one or more coatings that, in some instances, may facilitate formation of the vapor. For example, in some implementations, at least a portion of an outer surface (e.g., drop ejection surface) of the mesh plate may be coated with a hydrophobic coating. Additionally, or alternatively, in some implementations, at least a portion of an inner surface (e.g., liquid penetration surface) may be coated with a hydrophilic coating.

Figure 4A:
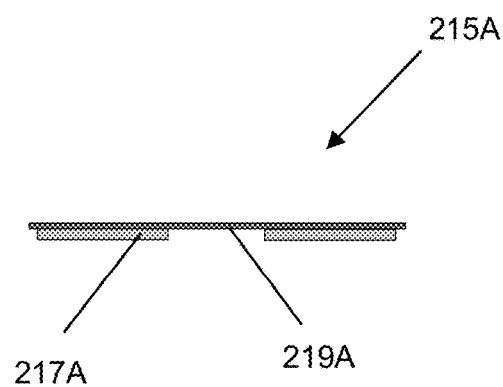
FIG. 4A illustrates a side schematic view of a portion of an atomization assembly, according to an example implementation of the present disclosure.
Figure 4B:
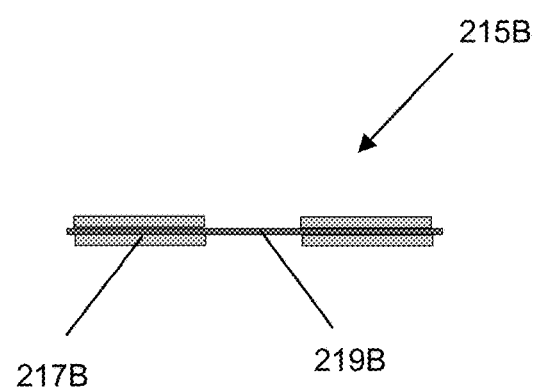
FIG. 4B illustrates a side schematic view of a portion of an atomization assembly, according to an example implementation of the present disclosure.
Figure 4C:
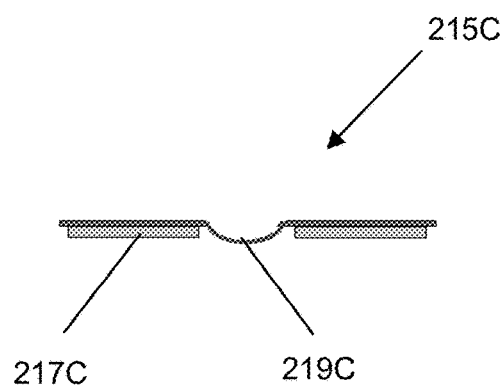
FIG. 4C illustrates a side schematic view of a portion of an atomization assembly, according to an example implementation of the present disclosure.
Figure 4D:
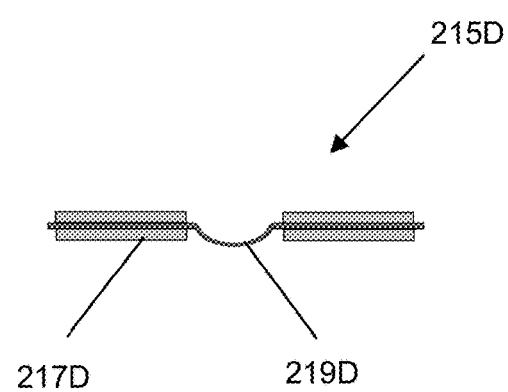
FIG. 4D illustrates a side schematic view of a portion of an atomization assembly, according to an example implementation of the present disclosure.
Figure 4E:
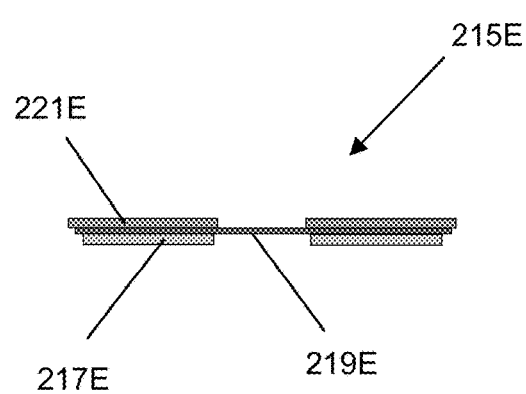
FIG. 4E illustrates a side schematic view of a portion of an atomization assembly, according to an example implementation of the present disclosure.
Figure 4F:
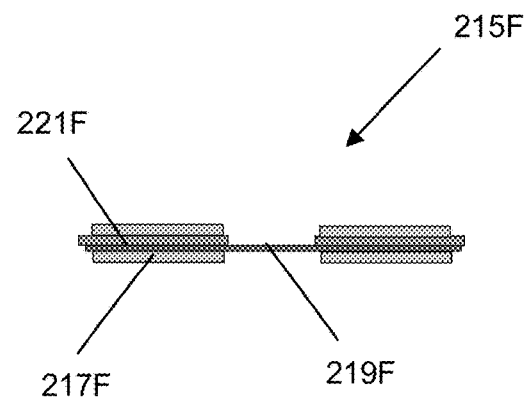
FIG. 4F illustrates a side schematic view of a portion of an atomization assembly, according to an example implementation of the present disclosure.

In various implementations, the structure of the atomization assembly may vary. For example, FIGS. 4A-4F illustrate example implementations of various atomization assemblies. In particular, FIG. 4A illustrates a side (or front, depending on point of reference) schematic view an atomization assembly comprising a piezoelectric ring 217A affixed to and substantially surrounding a mesh plate 219A. FIG. 4B illustrates an atomization assembly comprising a mesh plate 219A sandwiched between two portions of piezoelectric ring 217A. FIG. 4C illustrates an atomization assembly comprising a piezoelectric ring 217C affixed to and substantially surrounding a mesh plate 219C, wherein at least a portion of the mesh plate 219C is curved. FIG. 4D illustrates an atomization assembly comprising a mesh plate 219D sandwiched between two portions of a piezoelectric ring 217D, wherein at least a portion of the mesh plate 219D is curved. FIG. 4E illustrates an atomization assembly comprising a piezoelectric ring 217E affixed to and substantially surrounding one side of a mesh plate 219E, wherein the other side of the mesh plate 219E includes a metal ring 221E substantially surrounding and affixed thereto. FIG. 4F illustrates an atomization assembly comprising a mesh plate 219F one side of which includes a metal ring 221 F substantially surrounding and affixed thereto, the mesh plate 219F and metal ring 221F sandwiched between two portions of a piezoelectric ring 217F.

Referring back to FIG. 3, the mesh plate 219 includes a plurality of perforations. In some implementations, the perforations may be defined by circular openings in the surfaces of the plate. In other implementations, the perforations may be defined by non-circular openings in the plate, such as, for example, oval, rectangular, triangular, or regular or irregular polygon openings. In various implementations, the perforations may be created using a variety of different methods, including, but not limited to, via a laser (e.g., a femtosecond laser) or via electroplating (e.g., lithography, or focused ion beams) or via use of high or low energy ion or electron beams. In various implementations, the shapes defined through the plate by the perforations may vary. For example, in some implementations the shapes defined through the plate by the perforations may be substantially cylindrical. In other implementations, the shapes defined through the plate by the perforations may be substantially conical (e.g., having a truncated conical shape defining a smaller opening on one surface of the plate and a larger opening on the opposite surface of the plate). In other implementations, the shapes defined through the plate by the perforations may be tetragonal or pyramidal. It is believed that in some implementations, substantially conical shapes may increase the performance of the mesh in atomizing the liquid composition. Although any orientation of the mesh plate may be used, in some implementations with perforations defining substantially conical shapes through the plate, the larger opening may be located proximate the surface of the liquid composition and the smaller opening may define an aerosol outlet area. In some implementations with perforations defining substantially conical shapes, the smaller openings may have a size in the inclusive range of approximately 1 micron up to approximately 10 microns, with an average size of approximately 2 microns to approximately 5 microns. In other implementations, the smaller openings may have a size in the inclusive range of approximately several hundred nanometers up to approximately 4 microns, with an average size of approximately 2 microns to approximately 3.1 microns. In other implementations, the smaller openings may have a size in the inclusive range of approximately several hundred nanometers to approximately 2 microns, with an average size of approximately 1 micron. In some implementations, the larger openings may have a size in the inclusive range of approximately 10 microns to approximately 60 microns, with an average size of approximately 20 microns to approximately 30 microns. In other implementations, the larger openings may have a size in the inclusive range of approximately 5 microns to approximately 20 microns, with an average size of approximately 10 microns. In some implementations, the size of the perforations may be substantially uniform throughout the perforated portion of the plate; however, in other implementations, the size of the perforations may vary. In such a manner, the formed aerosol may have different size aerosol droplets. For example, in some implementations the perforations may be larger in one portion of the plate and smaller in another portion of the plate. Such portions may include, for example, the center of the plate and a periphery of the plate, or alternating rings that extend radially from the center of the plate.

In various implementations, the mesh plate may have any number of perforations. In some implementations, for example, a number of perforations in the mesh plate may be in the inclusive range of approximately 200 to approximately 6,000, with an average number of perforations of approximately 1,100 to approximately 2,500. In other implementations, a number of perforations in the mesh plate may be in the inclusive range of approximately 400 to approximately 1,000. In various implementations, the thickness of the piezoelectric ring and the thickness of the mesh plate may vary. For example, in some implementations the thickness of the mesh plate may be in the range of a few microns to a few millimeters. In various implementations, the overall diameter of a mesh plate may vary. For example, in some implementations the overall diameter of the mesh plate may be in the inclusive range of approximately a few millimeters to approximately 30 millimeters. In some implementations, the outer diameter of the piezoelectric ring may be larger than the overall diameter of the mesh plate. In other implementations, the outer diameter may be substantially the same size as the overall diameter of the mesh plate. In various implementations, the diameter of the perforation area may be smaller than the overall diameter of the mesh plate. For example, in some implementations the diameter of the perforated area may be in the inclusive range of approximately 1 millimeter to approximately 20 millimeters, with an average of approximately 4 millimeters to approximately 12 millimeters. In some implementations, the inner diameter of the piezoelectric ring may be larger than the diameter of the perforated area of the mesh plate. In other implementations, the inner diameter of the piezoelectric ring may be substantially the same as, or smaller than, the diameter of the perforated area of the mesh plate. In some implementations, the thickness of the piezoelectric ring may be in the inclusive range of a few hundred microns to tens of millimeters. For example, in some implementations the thickness of the piezoelectric ring may be smaller than 1 millimeter.

In various implementations, the piezoelectric ring may be made of a piezoceramic material. In general, piezoceramic materials possess piezoelectric properties (e.g., ferroelectric properties), wherein they are configured to change shape to a small extent (e.g., 1-2 microns) when exposed to an electrical stimulus. This occurs due to a shift in the crystal structure of the piezoceramic materials (e.g., from orthorhombic to cubic, or hexagonal to cubic, etc.). With respect to a piezoceramic ring, such a change in shape results in an internal strain and therefore shrinkage of the disc that results in bending of the disk due to its rigid structure. Because the ring is affixed to the mesh plate, the bending of the ring is transferred to the mesh material. When the electric current is disconnected from the piezoelectric ring, the ring and mesh plate return to their original shape and position. As such, a continuous change of the shape and position will result in an oscillating motion that can be used as a vibration source. In various implementations, the frequency of the piezoelectric ring may be in the range of a few Hz to several MHz. For example, in some implementations the frequency of the piezoelectric ring in in the inclusive range of approximately 50 KHz to approximately 150 KHz, with an average, in one implementation of approximately 110 KHz, in another implementation of approximately 113 KHz, and in another implementation, of approximately 117 KHz, in another implementation, of approximately 130 KHz, in another implementation, of approximately 150 KHz, in another implementation, of approximately 170 KHz, and in another implementation, of approximately 250 KHz. In other implementations, the frequency of the piezoelectric ring is in the inclusive range of approximately 1 MHz to approximately 5 MHz, with an average of approximately 3 MHz to approximately 3.5 MHz.

In various implementations of the present disclosure, a variety of different piezoelectric materials are possible, including natural or synthetic materials. Some non-limiting examples of natural piezoelectric materials include, for example, quartz, berlinite ($AlPO_4$), sucrose, rochelle salt, topaz, tourmaline-group minerals, lead titanate ($PbTiO_3$), and collagen. Some non-limiting examples of synthetic materials include, for example, a ($La_3Ga_5SiO_{14}$), gallium phosphate, gallium orthophosphate ($GaPO_4$), lithium niobate ($LiNbO_3$), lithium tantalate ($LiTaO_3$), AlN, ZnO, barium titanate ($BaTiO_3$), lead zirconate titanate ($Pb[Zr_x Ti_{1-x}]O_3$) (a.k.a. PZT), potassium niobate ($KNbO_3$), sodium tungstate ($Na_2WO_3$), $Ba_2NaNb_5O_5$, $Pb_2KNb_5O_{15}$, zinc oxide (ZnO), sodium potassium niobate ($(K,Na)NbO_3$) (a.k.a. NKN), bismuth ferrite ($BiFeO_3$), sodium niobate $NaNbO_3$, barium titanate ($BaTiO_3$), bismuth titanate $Bi_4Ti_3O_{12}$, sodium titanate, and sodium bismuth titanate $NaBi(TiO_3)_2$. In other implementations, polymers exhibiting piezoelectric characteristics may be used, including, but not limited to, polyvinylidene fluoride (PVDF).

In various implementations, the mesh plate 219 of the atomization assembly 215 may be in contact with at least a portion of a liquid composition, and/or may be proximate at least a portion of a liquid composition, and/or may receive (such as via a delivery mechanism) at least a portion of a liquid composition. In such a manner, the resulting vibration of the plate generates an aerosol from the liquid composition. In particular, in some implementations, the liquid composition is driven through the plurality of perforations resulting in the generation of a plurality of aerosol particles. Likewise, in other implementations, such as, for example, implementations in which the mesh plate is immersed in the liquid composition, vibration of the plate creates ultrasonic waves within the liquid composition that result in the formation of an aerosol at the surface of the liquid composition. As will be described in more detail below, in other implementations the liquid composition may be applied and/or transferred to the atomization assembly to create the aerosol.

Figure 5:
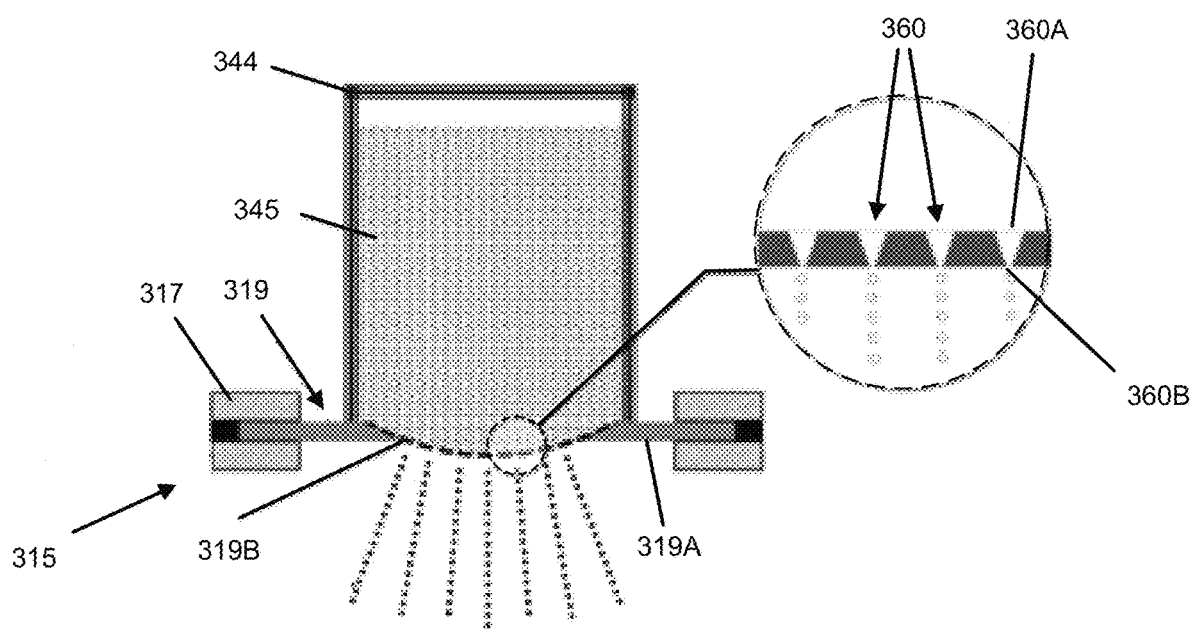
FIG. 5 illustrates a side schematic view of a portion of a reservoir configured to hold a liquid composition, and an atomization assembly configured to generate an aerosol from the liquid composition, according to an example implementation of the present disclosure.

Another example of an atomization assembly of one implementation is shown in FIG. 5. In particular, FIG. 5 illustrates a side (or front, depending on point of reference) schematic view of an atomization assembly 315 that comprises a piezoelectric ring 317 that is affixed to and substantially surrounds a mesh plate 319. As illustrated in the figure, the atomization assembly 315 is located proximate one end of a reservoir 344 containing a liquid composition 345. The mesh plate 319 of the depicted implementation includes two portions, an outer portion 319A that is substantially flat, and an inner portion 319 B that is domed. In the depicted implementation, inner domed portion 319B of the mesh plate 319 is configured to interact with the liquid composition 345 and has a convex configuration with respect to the reservoir 344 (and liquid composition 345). In the depicted implementation, the mesh plate 319 includes a plurality of perforations 360 that have a substantially conical shape. In particular, the plurality of perforations 360 include a larger end 360A, configured to be located proximate the interface with the liquid composition 345, and a smaller end 360B, through which the formed aerosol passes.

Figure 6A:
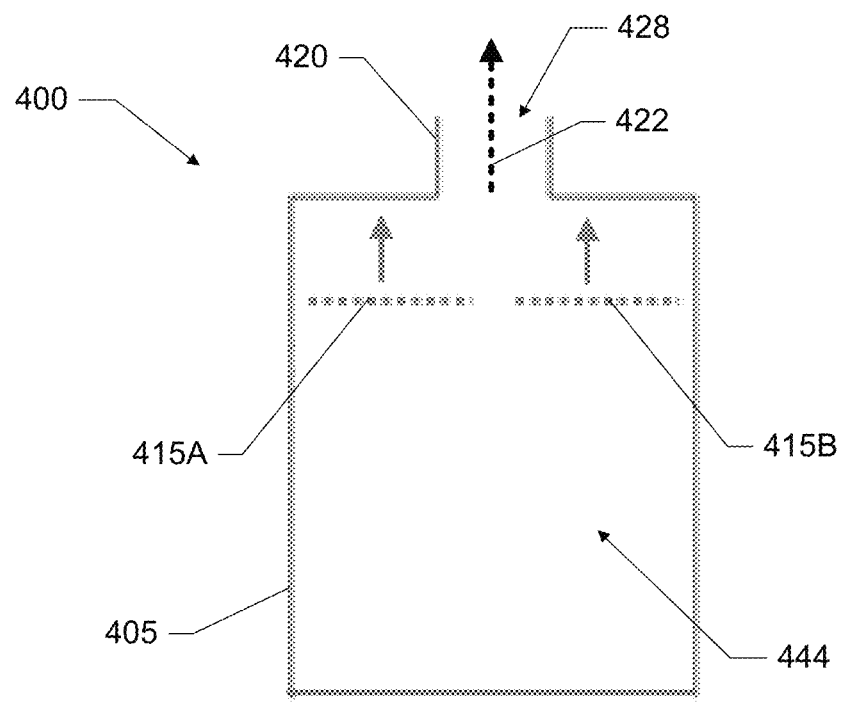
FIG. 6A illustrates a side schematic view of a portion of an aerosol delivery device, according to an example implementation of the present disclosure.
Figure 6B:
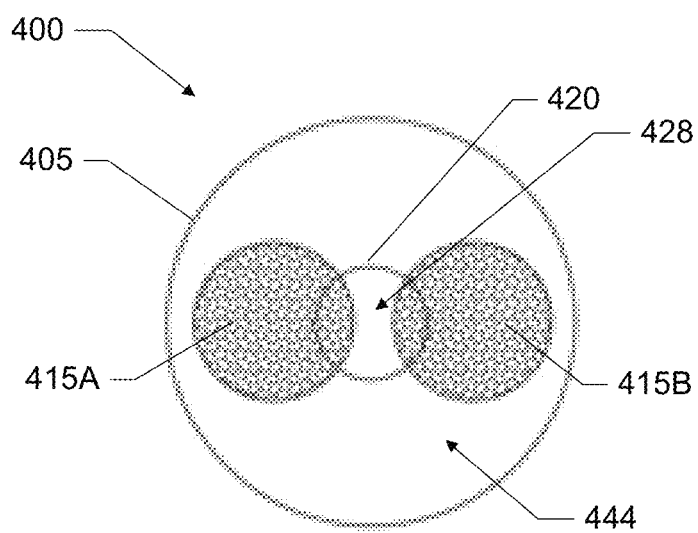
FIG. 6B illustrates a top schematic view of the portion of the aerosol delivery device of FIG. 5A.

In various implementations, it may be advantageous to include multiple atomization assemblies in a single aerosol delivery device. Along those lines, FIGS. 6A and 6B illustrate a portion of an aerosol delivery device, according to an example implementation of the present disclosure. In particular, FIG. 6A illustrates a side (or top, depending on point of reference) schematic view of a portion of an aerosol delivery device 400, and FIG. 6B illustrates a top (or front) schematic view of a portion of the aerosol delivery device 400. As depicted in the figures, the aerosol delivery device 400 includes a housing 405 that defines an outer wall. The aerosol delivery device 400 further includes a mouthpiece portion 420 through which the formed aerosol travels. In some implementations, the housing may define an inner surface, at least a portion of which may come in contact with the formed aerosol. In further implementations, the inner surface may be coated with a coating, such as, for example, a hydrophobic coating. In the depicted implementation, the mouthpiece portion 420 is substantially aligned with a center of the device and defines an opening 428 and an exit aerosol path 422. In other implementations, however, the components need not be aligned. The aerosol delivery device 400 of the depicted implementation also includes a reservoir 444 configured to contain a liquid composition (not shown).

The depicted implementation further includes a pair of atomization assemblies 415A, 415B that are in fluid communication (either directly or through one or more additional components) with the reservoir 444 and the liquid composition therein. Although other implementations may differ, in the depicted implementation each of the atomization assemblies 415A, 415B comprises a vibrating mesh assembly. In the depicted implementation, the vibrating mesh assembly comprises a piezoelectric material affixed to and substantially surrounding a mesh plate that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In various implementations, an electrical connection (not shown) connects the atomization assemblies to a control component and/or battery of the aerosol delivery device. In such a manner, the atomization assemblies 415A, 415B of the depicted implementation may be energized by the battery and/or control component so as to vibrate the mesh plate at a relatively high rate. Because at least a portion of the liquid composition is delivered to the mesh plate, the resulting vibration of the plate generates an aerosol from the liquid composition. Further reference is made to the discussion of vibrating mesh assembly components and variations described above.

Although other configurations are possible, the mesh plates of the atomization assemblies 415A, 415B of the depicted implementations have substantially circular shapes and are substantially evenly spaced on opposite sides of the exit aerosol path 422. Further, the mesh plates of the atomization assemblies 415A, 415B of the depicted implementation are substantially coplanar and substantially perpendicular to the exit aerosol path 422 defined by the mouthpiece portion 420. It should be noted that in some implementations, the mesh plates may be configured to vibrate at different frequencies, which, in some implementations, may occur at the same or different times. In addition, in some implementations the mesh plates may be associated with (e.g., located in or in fluid communication with) separate reservoirs, which may contain different liquid compositions.

Figure 7A:
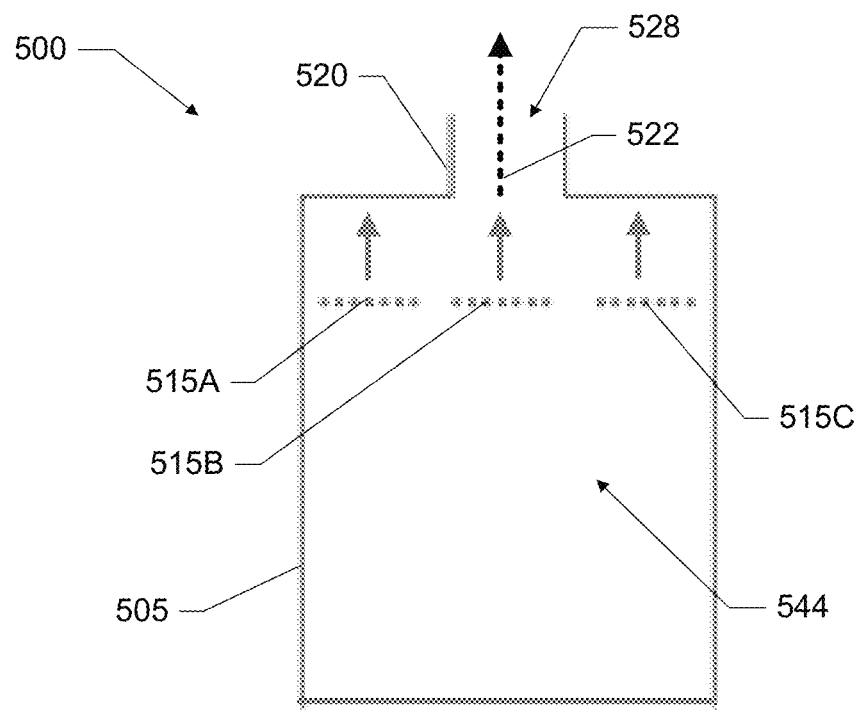
FIG. 7A illustrates a side schematic view of a portion of an aerosol delivery device, according to an example implementation of the present disclosure.
Figure 7B:
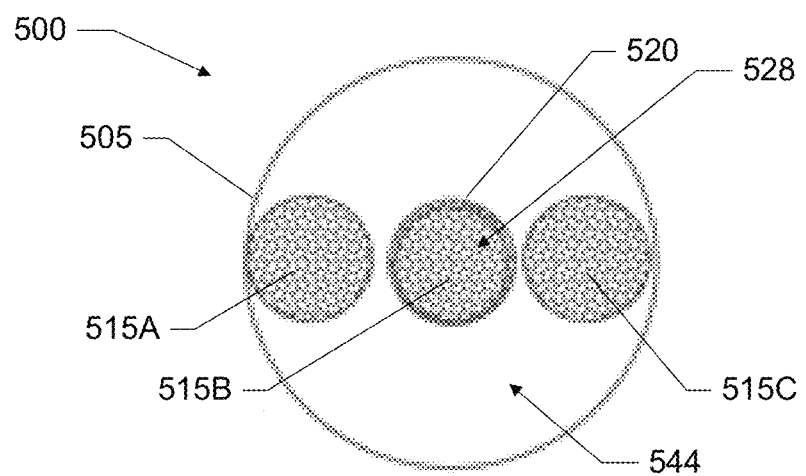
FIG. 7B illustrates a top schematic view of the portion of the aerosol delivery device of FIG. 6A.

FIGS. 7A and 7B illustrate a portion of an aerosol delivery device, according to another example implementation of the present disclosure. In particular, FIG. 7A illustrates a side (or top, depending on point of reference) schematic view of a portion of an aerosol delivery device 500, and FIG. 7B illustrates a top (or front) schematic view of a portion of the aerosol delivery device 500. As depicted in the figures, the aerosol delivery device 500 includes a housing 505 that defines an outer wall. The aerosol delivery device 500 further includes a mouthpiece portion 520 through which the formed aerosol travels. In some implementations, the housing may define an inner surface, at least a portion of which may come in contact with the formed aerosol. In further implementations, the inner surface may be coated with a coating, such as, for example, a hydrophobic coating. In the depicted implementation, the mouthpiece portion 520 is substantially aligned with a center of the device and defines an opening 528 and an exit aerosol path 522. The aerosol delivery device 500 of the depicted implementation also includes a reservoir 544 configured to contain a liquid composition (not shown).

The depicted implementation further includes three atomization assemblies 515A, 515B, 515C that are in fluid communication (either directly or through one or more additional components) with the reservoir 544 and the liquid composition therein. Although other implementations may differ, in the depicted implementation each of the atomization assemblies 515A, 515B, 515C comprises a vibrating mesh assembly. In the depicted implementation, the vibrating mesh assembly comprises a piezoelectric material affixed to and substantially surrounding a mesh plate that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In various implementations, an electrical connection (not shown) connects the atomization assemblies to a control component and/or battery of the aerosol delivery device. In such a manner, the atomization assemblies 515A, 515B, 515C of the depicted implementation may be energized by the battery and/or control component so as to vibrate the mesh plate at a relatively high rate. Because at least a portion of the liquid composition is delivered to the mesh plate, the resulting vibration of the plate generates an aerosol from the liquid composition. Further reference is made to the discussion of vibrating mesh assembly components and variations described above.

Although other configurations are possible, the mesh plates of the atomization assemblies 515A, 515B, 515C of the depicted implementations have substantially circular shapes and are substantially evenly spaced, with one mesh plate substantially aligned below the exit aerosol path 522, and the other two mesh plates on opposite sides of the exit aerosol path 522. Further, the mesh plates of the atomization assemblies 515A, 515B, 515C of the depicted implementation are substantially coplanar, substantially linearly aligned, and substantially perpendicular to the exit aerosol path 522 defined by the mouthpiece portion 520. It should be noted that in some implementations, the mesh plates may be configured to vibrate at different frequencies, which, in some implementations, may occur at the same or different times. In addition, in some implementations the mesh plates may be associated with (e.g., located in or in fluid communication with) separate reservoirs, which may contain different liquid compositions.

Figure 8A:
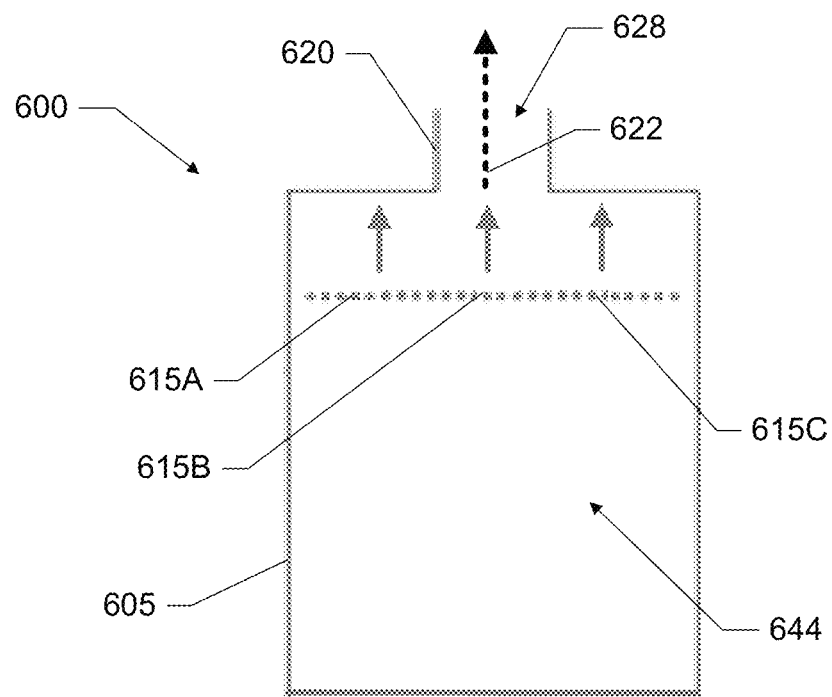
FIG. 8A illustrates a side schematic view of a portion of an aerosol delivery device, according to an example implementation of the present disclosure.
Figure 8B:
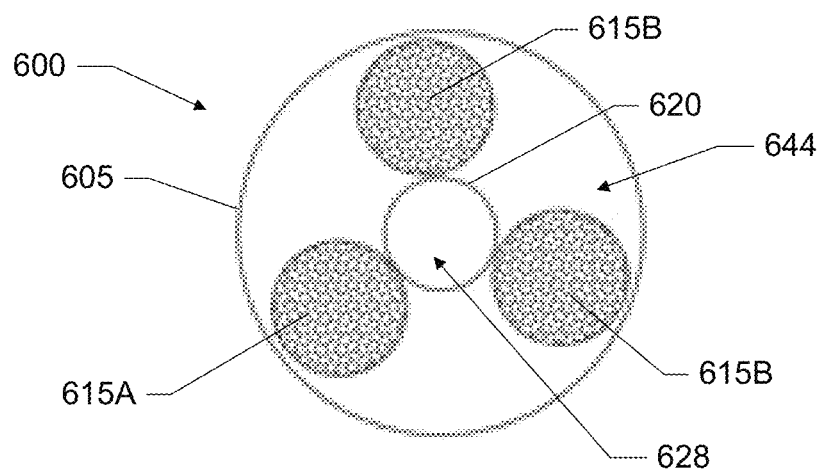
FIG. 8B illustrates a top schematic view of the portion of the aerosol delivery device of FIG. 8A.

FIGS. 8A and 8B illustrate a portion of an aerosol delivery device, according to another example implementation of the present disclosure. In particular, FIG. 8A illustrates a side (or top, depending on point of reference) schematic view of a portion of an aerosol delivery device 600, and FIG. 8B illustrates a top (or front) schematic view of a portion of the aerosol delivery device 600. As depicted in the figures, the aerosol delivery device 600 includes a housing 605 that defines an outer wall. The aerosol delivery device 600 further includes a mouthpiece portion 620 through which the formed aerosol travels. In some implementations, the housing may define an inner surface, at least a portion of which may come in contact with the formed aerosol. In further implementations, the inner surface may be coated with a coating, such as, for example, a hydrophobic coating. In the depicted implementation, the mouthpiece portion 620 is substantially aligned with a center of the device and defines an opening 628 and an exit aerosol path 622. The aerosol delivery device 600 of the depicted implementation also includes a reservoir 644 configured to contain a liquid composition (not shown).

The depicted implementation further includes three atomization assemblies 615A, 615B, 615C that are in fluid communication (either directly or through one or more additional components) with the reservoir 644 and the liquid composition therein. Although other implementations may differ, in the depicted implementation each of the atomization assemblies 615A, 615B, 615C comprises a vibrating mesh assembly. In the depicted implementation, the vibrating mesh assembly comprises a piezoelectric material affixed to and substantially surrounding a mesh plate that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In various implementations, an electrical connection (not shown) connects the atomization assemblies to a control component and/or battery of the aerosol delivery device. In such a manner, the atomization assemblies 615A, 615B, 615C of the depicted implementation may be energized by the battery and/or control component so as to vibrate the mesh plate at a relatively high rate. Because at least a portion of the liquid composition is delivered to the mesh plate, the resulting vibration of the plate generates an aerosol from the liquid composition. Further reference is made to the discussion of vibrating mesh assembly components and variations described above.

Although other configurations are possible, the mesh plates of the atomization assemblies 615A, 615B, 615C of the depicted implementations have substantially circular shapes and are radially spaced about a center of the device. In particular, the mesh plates of the atomization assemblies 615A, 615B, 615C are substantially evenly radially spaced about the center of the device. Further, the mesh plates of the atomization assemblies 615A, 615B, 615C of the depicted implementation are substantially coplanar and substantially perpendicular to the exit aerosol path 622 defined by the mouthpiece portion 620. It should be noted that in some implementations the atomization assemblies need not be evenly spaced around a center of the device. It should also be noted that in some implementations the atomization assemblies need not be substantially co-planar. It should further be noted that in some implementations the mesh plates may be configured to vibrate at different frequencies, which, in some implementations, may occur at the same or different times. In addition, in some implementations the mesh plates may be associated with (e.g., located in or in fluid communication with) separate reservoirs, which may contain different liquid compositions.

Figure 9:
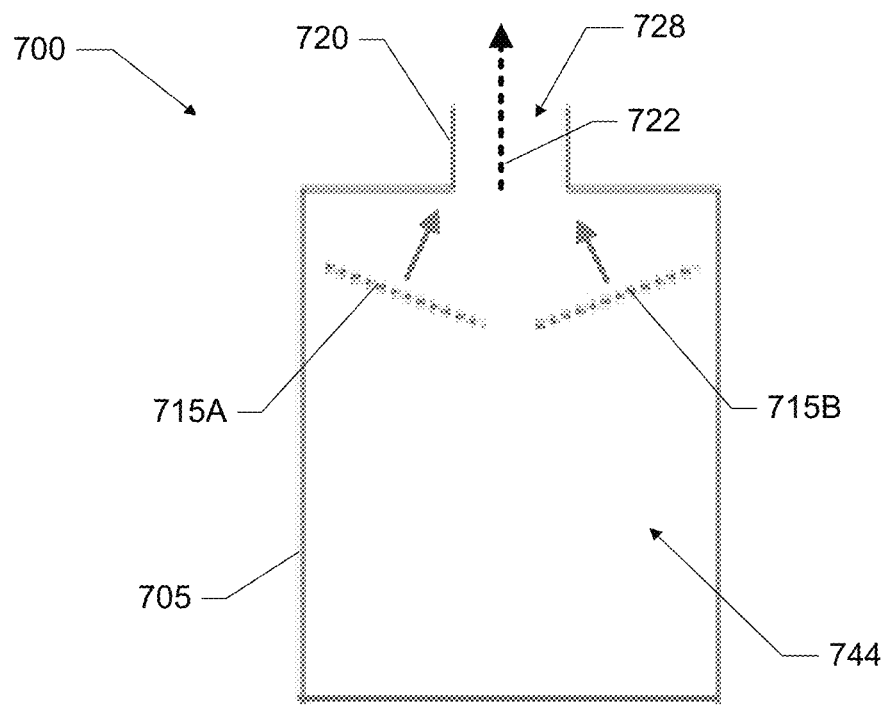
FIG. 9 illustrates a side schematic view of a portion of an aerosol delivery device, according to an example implementation of the present disclosure.

FIG. 9 illustrates a portion of an aerosol delivery device, according to another example implementation of the present disclosure. In particular, FIG. 9 illustrates a side (or top, depending on point of reference) schematic view of a portion of an aerosol delivery device 700. As depicted in the figure, the aerosol delivery device 700 includes a housing 705 that defines an outer wall. The aerosol delivery device 700 further includes a mouthpiece portion 720 through which the formed aerosol travels. In some implementations, the housing may define an inner surface, at least a portion of which may come in contact with the formed aerosol. In further implementations, the inner surface may be coated with a coating, such as, for example, a hydrophobic coating. In the depicted implementation, the mouthpiece portion 720 is substantially aligned with a center of the device and defines an opening 728 and an exit aerosol path 722. The aerosol delivery device 700 of the depicted implementation also includes a reservoir 744 configured to contain a liquid composition (not shown).

The depicted implementation further includes a pair of atomization assemblies 715A, 715B that are in fluid communication (either directly or through one or more additional components) with the reservoir 744 and the liquid composition therein. Although other implementations may differ, in the depicted implementation each of the atomization assemblies 715A, 715B comprises a vibrating mesh assembly. In the depicted implementation, the vibrating mesh assembly comprises a piezoelectric material affixed to and substantially surrounding a mesh plate that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In various implementations, an electrical connection (not shown) connects the atomization assemblies to a control component and/or battery of the aerosol delivery device. In such a manner, the atomization assemblies 715A, 715B of the depicted implementation may be energized by the battery and/or control component so as to vibrate the mesh plate at a relatively high rate. Because at least a portion of the liquid composition is delivered to the mesh plate, the resulting vibration of the plate generates an aerosol from the liquid composition. Further reference is made to the discussion of vibrating mesh assembly components and variations described above.

Although other configurations are possible, the mesh plates of the atomization assemblies 715A, 715B of the depicted implementation are substantially evenly spaced and on opposite sides of the exit aerosol path 722. Further, the mesh plates of the atomization assemblies 715A, 715B of the depicted implementation are angled with respect to the exit aerosol path 722. Although in the depicted implementation, both mesh plates are angled with respect to the exit aerosol path 772 at substantially the same acute angle, in some implementations one of the mesh plates may be angled (e.g., at an acute or obtuse angle) with respect to the exit aerosol path and another mesh plate may be substantially perpendicular to the exit aerosol path. In other implementations, one of the mesh plates may be angled (e.g., at an acute or obtuse angle) with respect to the exit aerosol path and another mesh plate may be substantially aligned with the exit aerosol path. In other implementations, one mesh plate may be angled with respect to the exit aerosol path at a first angle (e.g., acute, obtuse, or substantially perpendicular) and another mesh plate may be angled (e.g., acute, obtuse, or substantially perpendicular) with respect to the exit aerosol path at a different angle. The mesh plates of the atomization assemblies 715A, 715B of the depicted implementation are angled toward each other, with each mesh plate defining an acute angle with respect to the exit aerosol path 722 (e.g., an acute angle with respect to the portion of the exit aerosol path proximate the opening 728). It should be noted that in some implementations, the atomization assemblies need not be evenly spaced. It should also be noted that in some implementations, the atomization assemblies may have different angles with respect to the exit aerosol path. It should further be noted that in some implementations, the mesh plates may be configured to vibrate at different frequencies, which, in some implementations, may occur at the same or different times. In addition, in some implementations the mesh plates may be associated with (e.g., located in or in fluid communication with) separate reservoirs, which may contain different liquid compositions.

It should be noted that in some implementations, as an alternative to arranging an atomization assembly or assemblies at an angle (or in addition thereto), an aerosol delivery device in accordance with the present disclosure may include one or more angled features that deflect the flow of aerosol particles leaving the atomization assembly or assemblies before exiting the device. For example, in some implementations, the mouthpiece portion may include at least one deflection feature (such as, for example, a baffle, a wall, a flange, etc.) that is angled with respect to the direction of flow of aerosol particles leaving the atomization assembly or assemblies. In other implementations, the deflection feature need not be included in the mouthpiece portion and may be located in any location between the atomization assembly or assemblies and the mouthpiece portion. In various implementations, the deflection feature may have any angle with respect to the direction of flow of aerosol particles directed toward the feature, including a substantially perpendicular angle, as well as any acute angle, or any obtuse angle. In some implementations, the deflection feature may be arranged at an angle of approximately 45 degrees with respect to the direction of aerosol flow directed toward the feature. In other implementation, the deflection feature may be arranged at an angle of approximately 60 degrees with respect to the direction of aerosol flow directed toward the feature. In other implementations, the deflection feature may be arranged at an angle of approximately 75 degrees with respect to the direction of aerosol flow directed toward the feature. In other implementations, the deflection feature may be arranged at an angle of approximately 90 degrees with respect to the direction of aerosol flow directed toward the feature. In some implementations, the deflection feature may include one or more channels extending through the deflection feature. Although other configurations are possible, in some implementations, the one or more channels may be substantially parallel to the direction of aerosol flow directed toward the feature.

Figure 10:
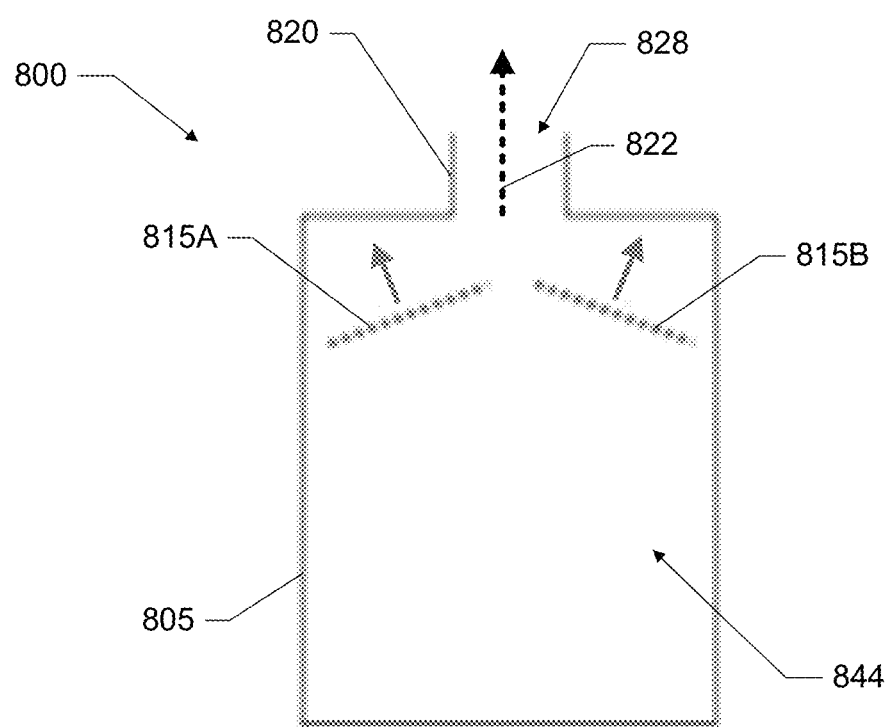
FIG. 10 illustrates a side schematic view of a portion of an aerosol delivery device, according to an example implementation of the present disclosure.

FIG. 10 illustrates a portion of an aerosol delivery device, according to another example implementation of the present disclosure. In particular, FIG. 10 illustrates a side (or top, depending on point of reference) schematic view of a portion of an aerosol delivery device 800. As depicted in the figure, the aerosol delivery device 800 includes a housing 805 that defines an outer wall. The aerosol delivery device 800 further includes a mouthpiece portion 820 through which the formed aerosol travels. In some implementations, the housing may define an inner surface, at least a portion of which may come in contact with the formed aerosol. In further implementations, the inner surface may be coated with a coating, such as, for example, a hydrophobic coating. In the depicted implementation, the mouthpiece portion 820 is substantially aligned with a center of the device and defines an opening 828 and an exit aerosol path 822. The aerosol delivery device 800 of the depicted implementation also includes a reservoir 844 configured to contain a liquid composition (not shown).

The depicted implementation further includes a pair of atomization assemblies 815A, 815B that are in fluid communication (either directly or through one or more additional components) with the reservoir 844 and the liquid composition therein. Although other implementations may differ, in the depicted implementation each of the atomization assemblies 815A, 815B comprises a vibrating mesh assembly. In the depicted implementation, the vibrating mesh assembly comprises a piezoelectric material affixed to and substantially surrounding a mesh plate that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In various implementations, an electrical connection (not shown) connects the atomization assemblies to a control component and/or battery of the aerosol delivery device. In such a manner, the atomization assemblies 815A, 815B of the depicted implementation may be energized by the battery and/or control component so as to vibrate the mesh plate at a relatively high rate. Because at least a portion of the liquid composition is delivered to the mesh plate, the resulting vibration of the plate generates an aerosol from the liquid composition. Further reference is made to the discussion of vibrating mesh assembly components and variations described above.

Although other configurations are possible, the mesh plates of the atomization assemblies 815A, 815B of the depicted implementation are substantially evenly spaced and on opposite sides of the exit aerosol path 822. Further, the mesh plates of the atomization assemblies 815A, 815B of the depicted implementation are angled with respect to the exit aerosol path 822. In particular, the mesh plates of the atomization assemblies 815A, 815B of the depicted implementation are angled away each other, with each mesh plate defining an obtuse angle with respect to the exit aerosol path 822 (e.g., an obtuse angle with respect to the portion of the exit aerosol path 822 proximate the opening 828). It should be noted that in some implementations, the mesh plates may be configured to vibrate at different frequencies, which, in some implementations, may occur at the same or different times. In addition, in some implementations the mesh plates may be associated with (e.g., located in or in fluid communication with) separate reservoirs, which may contain different liquid compositions.

Figure 11:
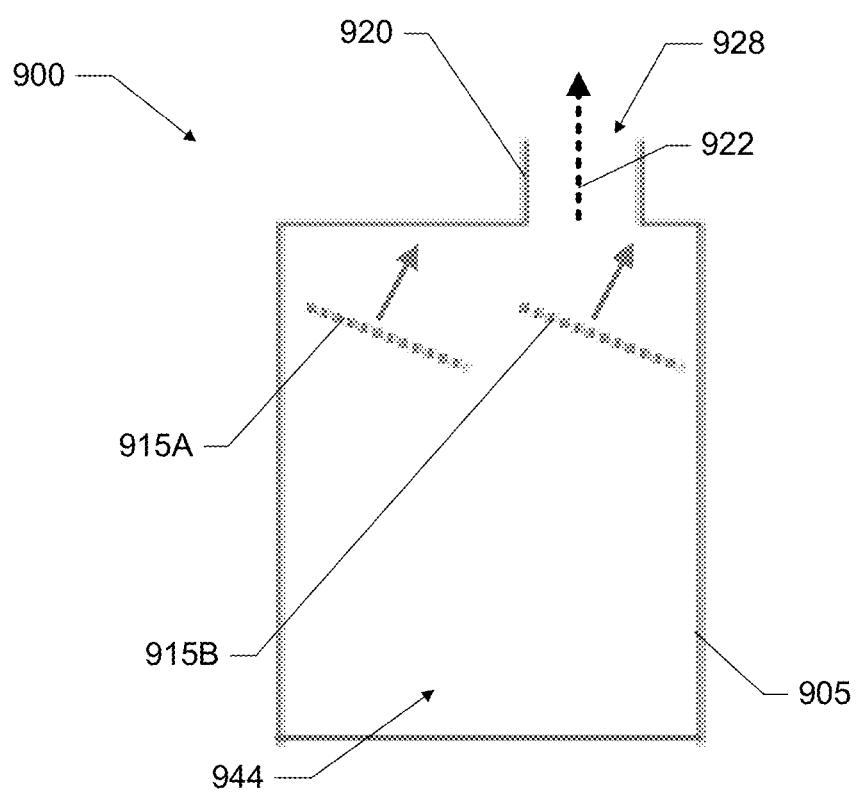
FIG. 11 illustrates a side schematic view of a portion of an aerosol delivery device, according to an example implementation of the present disclosure.

FIG. 11 illustrates a portion of an aerosol delivery device, according to another example implementation of the present disclosure. In particular, FIG. 11 illustrates a side (or top, depending on point of reference) schematic view of a portion of an aerosol delivery device 900. As depicted in the figure, the aerosol delivery device 900 includes a housing 905 that defines an outer wall. The aerosol delivery device 900 further includes a mouthpiece portion 920 through which the formed aerosol travels. In some implementations, the housing may define an inner surface, at least a portion of which may come in contact with the formed aerosol. In further implementations, the inner surface may be coated with a coating, such as, for example, a hydrophobic coating. In the depicted implementation, the mouthpiece portion 920 is offset from the center of the device (e.g., closer to one side of the device than another side of the device) and defines an opening 928 and an exit aerosol path 922. The aerosol delivery device 900 of the depicted implementation also includes a reservoir 944 configured to contain a liquid composition (not shown).

The depicted implementation further includes a pair of atomization assemblies 915A, 915B that are in fluid communication (either directly or through one or more additional components) with the reservoir 944 and the liquid composition therein. Although other implementations may differ, in the depicted implementation each of the atomization assemblies 915A, 915B comprises a vibrating mesh assembly. In the depicted implementation, the vibrating mesh assembly comprises a piezoelectric material affixed to and substantially surrounding a mesh plate that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In various implementations, an electrical connection (not shown) connects the atomization assemblies to a control component and/or battery of the aerosol delivery device. In such a manner, the atomization assemblies 915A, 915B of the depicted implementation may be energized by the battery and/or control component so as to vibrate the mesh plate at a relatively high rate. Because at least a portion of the liquid composition is delivered to the mesh plate, the resulting vibration of the plate generates an aerosol from the liquid composition. Further reference is made to the discussion of vibrating mesh assembly components and variations described above.

Although other configurations are possible, the mesh plates of the atomization assemblies 915A, 915B of the depicted implementation are substantially parallel. Further, the mesh plates of the atomization assemblies 915A, 915B of the depicted implementation are angled with respect to the exit aerosol path 922. In particular, the mesh plates of the atomization assemblies 915A, 915B of the depicted implementation are angled toward the offset mouthpiece portion 920, with each mesh plate defining an acute angle with respect to the exit aerosol path 922 (e.g., an acute angle with respect to the portion of the exit aerosol path 922 proximate the opening 928). It should be noted that in some implementations, the mesh plates may be configured to vibrate at different frequencies, which, in some implementations, may occur at the same or different times. In addition, in some implementations the mesh plates may be associated with (e.g., located in or in fluid communication with) separate reservoirs, which may contain different liquid compositions.

Figure 12:
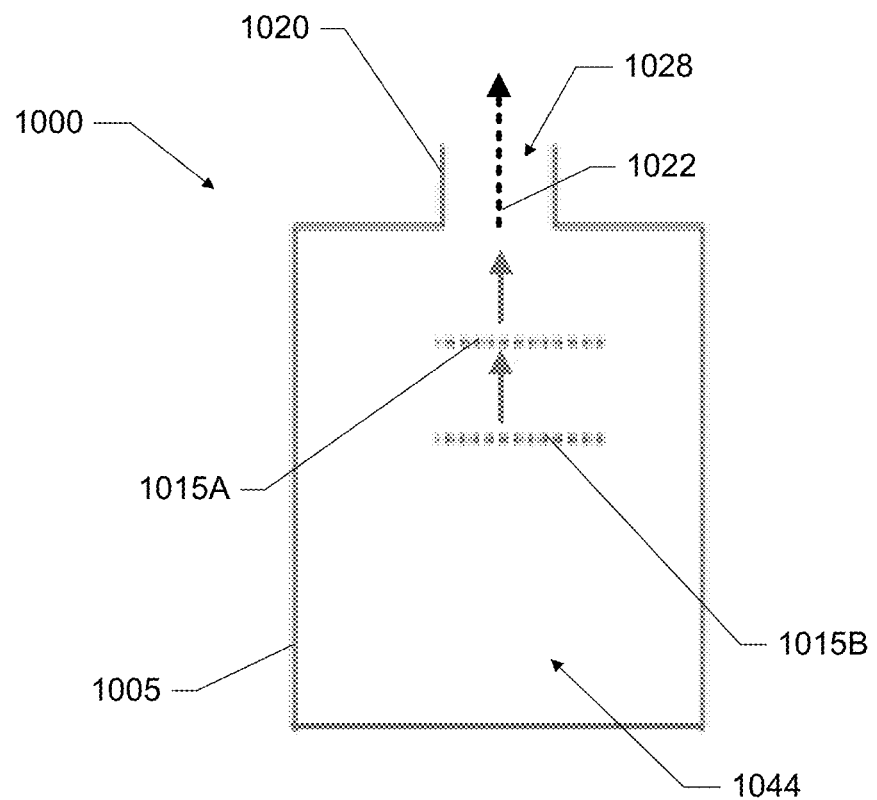
FIG. 12 illustrates a side schematic view of a portion of an aerosol delivery device, according to an example implementation of the present disclosure.

FIG. 12 illustrates a portion of an aerosol delivery device, according to another example implementation of the present disclosure. In particular, FIG. 11 illustrates a side (or top, depending on point of reference) schematic view of a portion of an aerosol delivery device 1000. As depicted in the figure, the aerosol delivery device 1000 includes a housing 1005 that defines an outer wall. The aerosol delivery device 1000 further includes a mouthpiece portion 1020 through which the formed aerosol travels. In some implementations, the housing may define an inner surface, at least a portion of which may come in contact with the formed aerosol. In further implementations, the inner surface may be coated with a coating, such as, for example, a hydrophobic coating. In the depicted implementation, the mouthpiece portion 1020 is substantially aligned with a center of the device and defines an opening 1028 and an exit aerosol path 1022. The aerosol delivery device 1000 of the depicted implementation also includes a reservoir 1044 configured to contain a liquid composition (not shown).

The depicted implementation further includes a pair of atomization assemblies 1015A, 1015B that are in fluid communication (either directly or through one or more additional components) with the reservoir 1044 and the liquid composition therein. It should be noted that in some implementations, only one of the atomization assemblies may be in fluid communication with the liquid composition. For example, in some implementations one atomization assembly may be in fluid communication with the liquid composition and may aerosolize the liquid composition onto the second atomization assembly, such as, for example, to create a thin film of liquid composition on the second atomization assembly. In such a manner, the second atomization assembly may re-aerosolize the thin film of liquid composition. As such, in some implementations, leakage and/or the particle size of the final aerosol may be reduced. In one implementation, the mesh plates of the atomization assemblies may have perforations having the same shape and same size. In other implementations, however, the mesh plates of the atomization assemblies may have different sizes and/or different shapes.

Although other implementations may differ, in the depicted implementation each of the atomization assemblies 1015A, 1015B comprises a vibrating mesh assembly. In the depicted implementation, the vibrating mesh assembly comprises a piezoelectric material affixed to and substantially surrounding a mesh plate that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In various implementations, an electrical connection (not shown) connects the atomization assemblies to a control component and/or battery of the aerosol delivery device. In such a manner, the atomization assemblies 1015A, 1015B of the depicted implementation may be energized by the battery and/or control component so as to vibrate the mesh plate at a relatively high rate. Because at least a portion of the liquid composition is delivered to the mesh plate, the resulting vibration of the plate generates an aerosol from the liquid composition. Further reference is made to the discussion of vibrating mesh assembly components and variations described above.

Although other configurations are possible, the mesh plates of the atomization assemblies 1015A, 1015B of the depicted implementation are substantially parallel. Further, the mesh plates of the atomization assemblies 1015A, 1015B of the depicted implementation are angled with respect to the exit aerosol path 1022. In particular, the mesh plates of the atomization assemblies 1015A, 1015B of the depicted implementation are positioned one above the other, with each mesh plate being substantially perpendicular to the exit aerosol path 1022. It should be noted that in some implementations, the mesh plates may be configured to vibrate at different frequencies, which, in some implementations, may occur at the same or different times. In addition, in some implementations the mesh plates may be associated with (e.g., located in or in fluid communication with) separate reservoirs, which may contain different liquid compositions.

Figure 13:
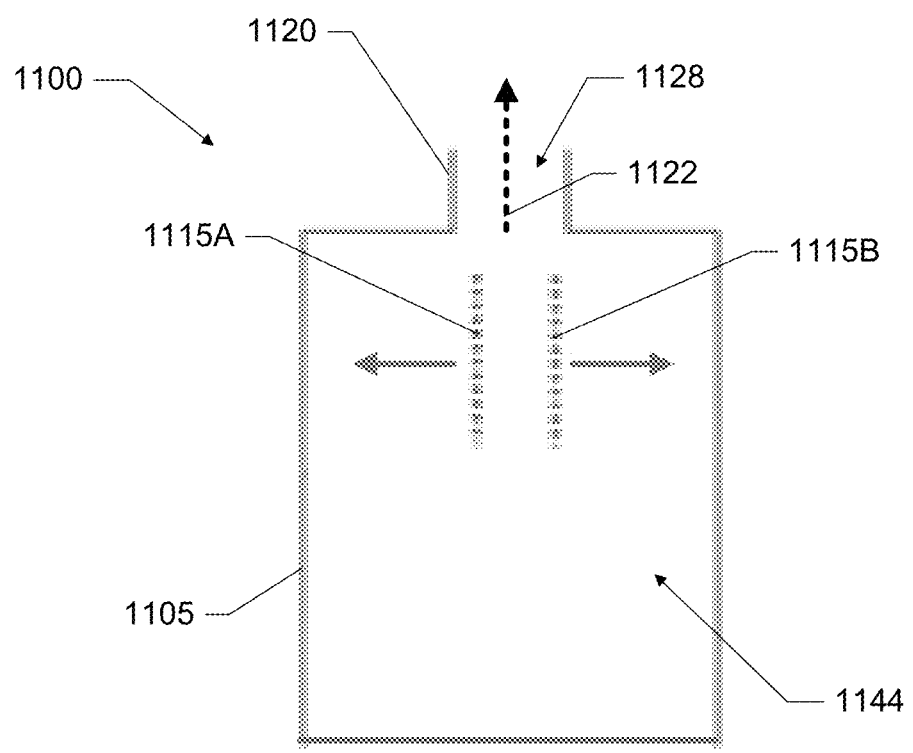
FIG. 13 illustrates a side schematic view of a portion of an aerosol delivery device, according to an example implementation of the present disclosure.

FIG. 13 illustrates a portion of an aerosol delivery device, according to another example implementation of the present disclosure. In particular, FIG. 12 illustrates a side (or top, depending on point of reference) schematic view of a portion of an aerosol delivery device 1100. As depicted in the figure, the aerosol delivery device 1100 includes a housing 1105 that defines an outer wall. The aerosol delivery device 1100 further includes a mouthpiece portion 1120 through which the formed aerosol travels. In some implementations, the housing may define an inner surface, at least a portion of which may come in contact with the formed aerosol. In further implementations, the inner surface may be coated with a coating, such as, for example, a hydrophobic coating. In the depicted implementation, the mouthpiece portion 1120 is substantially aligned with a center of the device and defines an opening 1128 and an exit aerosol path 1122. The aerosol delivery device 1100 of the depicted implementation also includes a reservoir 1144 configured to contain a liquid composition (not shown).

The depicted implementation further includes a pair of atomization assemblies 1115A, 1115B that are in fluid communication (either directly or through one or more additional components) with the reservoir 1144 and the liquid composition therein. Although other implementations may differ, in the depicted implementation each of the atomization assemblies 1115A, 1115B comprises a vibrating mesh assembly. In the depicted implementation, the vibrating mesh assembly comprises a piezoelectric material affixed to and substantially surrounding a mesh plate that is vibrated within the liquid composition or proximate the surface of the liquid composition to generate an aerosol. In some implementations, the liquid composition may be delivered to the mesh plate (such as, for example, via a one or more liquid transport elements, and/or another delivery device such as a micropump). In various implementations, an electrical connection (not shown) connects the atomization assemblies to a control component and/or battery of the aerosol delivery device. In such a manner, the atomization assemblies 1115A, 1115B of the depicted implementation may be energized by the battery and/or control component so as to vibrate the mesh plate at a relatively high rate. Because at least a portion of the liquid composition is delivered to the mesh plate, the resulting vibration of the plate generates an aerosol from the liquid composition. Further reference is made to the discussion of vibrating mesh assembly components and variations described above.

Although other implementations are possible, the mesh plates of the atomization assemblies 1115A, 1115B of the depicted implementation are substantially parallel. In particular, the mesh plates of the atomization assemblies 1115A, 1115B of the depicted implementation are substantially evenly spaced on opposite sides of the exit aerosol path 1122 and are substantially aligned with the exit aerosol path 1122. In the depicted implementation, the atomization assemblies 1115A, 1115B drive the generated aerosol outward and away from a center of the device. In other implementations, however, atomization assemblies may drive the generated aerosol toward a center of the device. In still other implementations, one atomization assembly may drive the generated aerosol outward and away from the center of the device, and another atomization assembly may direct the generated aerosol toward the center of the device. It should be noted that in some implementations, the mesh plates may be configured to vibrate at different frequencies, which, in some implementations, may occur at the same or different times. In addition, in some implementations the mesh plates may be associated with (e.g., located in or in fluid communication with) separate reservoirs, which may contain different liquid compositions.

Although in some implementations of the present disclosure a cartridge and a control unit may be provided together as a complete aerosol delivery device generally, these components may be provided separately. For example, the present disclosure also encompasses a disposable unit for use with a reusable unit. In specific implementations, such a disposable unit (which may be a cartridge as illustrated in the appended figures) can be configured to engage a reusable unit (which may be a control unit as illustrated in the appended figures). In still other configurations, a cartridge may comprise a reusable unit and a control unit may comprise a disposable unit.

Although some figures described herein illustrate a cartridge and a control unit in a working relationship, it is understood that the cartridge and the control unit may exist as individual components. Accordingly, any discussion otherwise provided herein in relation to the components in combination also should be understood as applying to the control unit and the cartridge as individual and separate components.

In another aspect, the present disclosure may be directed to kits that provide a variety of components as described herein. For example, a kit may comprise a control unit with one or more cartridges. A kit may further comprise a control unit with one or more charging components. A kit may further comprise a control unit with one or more batteries. A kit may further comprise a control unit with one or more cartridges and one or more charging components and/or one or more batteries. In further implementations, a kit may comprise a plurality of cartridges. A kit may further comprise a plurality of cartridges and one or more batteries and/or one or more charging components. In the above implementations, the cartridges or the control units may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:
a housing defining an outer wall, and further including a power source and a control component;
a tank portion located in the housing or configured to be connected therewith that includes a reservoir configured to contain a liquid composition;
an atomization assembly located in the housing or configured to be connected therewith configured to vaporize the liquid composition to generate an aerosol; and
an exit aerosol path in fluid communication with the atomization assembly and defining an opening,
wherein the atomization assembly comprises two or more vibrating assemblies, at least one of which is in fluid communication with the reservoir, wherein each vibrating assembly includes a mesh plate, wherein the mesh plates are substantially coplanar, and wherein the mesh plates are substantially perpendicular to the exit aerosol path.

2. The aerosol delivery device of claim 1, wherein the mesh plates are substantially linearly aligned.

3. The aerosol delivery device of claim 1, wherein there are three vibrating assemblies.

4. The aerosol delivery device of claim 3, wherein the mesh plates of the three vibrating assemblies are substantially linearly aligned.

5. The aerosol delivery device of claim 3, wherein the mesh plates of the three vibrating assemblies are radially spaced about a center of the device.

6. The aerosol delivery device of claim 5, wherein the mesh plates of the three vibrating assemblies are substantially evenly spaced.

7. The aerosol delivery device of claim 1, wherein the housing defines an inner surface, and wherein at least a portion of the inner surface is coated with a hydrophobic coating.

8. The aerosol delivery device of claim 1, wherein each of the vibrating assemblies further includes a piezoelectric ring affixed to and substantially surrounding the mesh plate.

9. The aerosol delivery device of claim 1, wherein each of the mesh plates is substantially flat.

10. The aerosol delivery device of claim 1, wherein at least a portion of each of the mesh plates is convex with respect to the reservoir.

11. The aerosol delivery device of claim 1 further comprising a mouthpiece portion, wherein the opening is defined in the mouthpiece portion.

12. An aerosol delivery device comprising:
a housing defining an outer wall, and further including a power source and a control component;
a tank portion located in the housing or configured to connected therewith that includes a reservoir configured to contain a liquid composition;
an atomization assembly located in the housing or configured to be connected therewith configured to vaporize the liquid composition to generate an aerosol; and
an exit aerosol path in fluid communication with the atomization assembly and defining an opening,
wherein the atomization assembly comprises two or more vibrating assemblies, at least one of which is in fluid communication with the reservoir, wherein each vibrating assembly includes a mesh plate, and wherein the mesh plates are substantially non-coplanar.

13. The aerosol delivery device of claim 12, wherein there are two vibrating assemblies, wherein the mesh plates of the vibrating assemblies are located on opposite sides of the exit aerosol path, and wherein at least one of the mesh plates of the vibrating assemblies defines an acute angle with respect to a portion of the exit aerosol path proximate the opening.

14. The aerosol delivery device of claim 12, wherein there are two vibrating assemblies, wherein the mesh plates of the vibrating assemblies are located on opposite sides of the exit aerosol path, and wherein at least one of the mesh plates of the vibrating assemblies defines an obtuse angle with respect to a portion of the exit aerosol path proximate the opening.

15. The aerosol delivery device of claim 12, wherein there are two vibrating assemblies, wherein the opening is offset from the center of the device, wherein the mesh plates of the vibrating assemblies are substantially parallel, and wherein each of the mesh plates of the vibrating assemblies defines an acute angle with respect to a portion of the exit aerosol path proximate the opening.

16. The aerosol delivery device of claim 15, wherein the mesh plates of the vibrating assemblies are angled toward the opening.

17. The aerosol delivery device of claim 12, wherein there are two vibrating assemblies, wherein the mesh plates of the vibrating assemblies are substantially parallel and are positioned one above the other, and wherein the mesh plates of the vibrating assemblies are substantially perpendicular to the exit aerosol path.

18. The aerosol delivery device of claim 17, wherein both of the vibrating assemblies are in fluid communication with the liquid composition.

19. The aerosol delivery device of claim 18, wherein a first one of the vibrating assemblies is in fluid communication with the liquid composition and is configured to generate a first aerosol, wherein the first aerosol creates a thin film on a second one of the vibrating assemblies, and wherein the second one of the vibrating assemblies is configured to re-aerosolize the thin film of liquid composition to generate a second aerosol.

20. The aerosol delivery device of claim 12, wherein there are two vibrating assemblies, and wherein the mesh plates of the vibrating assemblies are substantially parallel to the exit aerosol path.

21. The aerosol delivery device of claim 12, wherein the housing defines an inner surface, and wherein at least a portion of the inner surface is coated with a hydrophobic coating.

22. The aerosol delivery device of claim 12, wherein each of the vibrating assemblies further includes a piezoelectric ring affixed to and substantially surrounding the mesh plate.

23. The aerosol delivery device of claim 12, wherein each of the mesh plates is substantially flat.

24. The aerosol delivery device of claim 12, wherein at least a portion of each of the mesh plates is convex with respect to the reservoir.

25. The aerosol delivery device of claim 12 further comprising a mouthpiece portion, wherein the opening is defined in the mouthpiece portion.

* * * * *